United States Patent
Guevremont et al.

(10) Patent No.: US 7,045,778 B2
(45) Date of Patent: *May 16, 2006

(54) APPARATUS AND METHOD FOR ESTABLISHING A TEMPERATURE GRADIENT WITHIN A FAIMS ANALYZER REGION

(75) Inventors: Roger Guevremont, Ottawa (CA); Edward Masionis, Toronto (CA); David Barnett, Ottawa (CA)

(73) Assignee: Ionalytics Corporation, Ottawa (CA)

(*) Notice: Subject to any disclaimer, the term of this patent is extended or adjusted under 35 U.S.C. 154(b) by 0 days.

This patent is subject to a terminal disclaimer.

(21) Appl. No.: 11/038,099

(22) Filed: Jan. 21, 2005

(65) Prior Publication Data

US 2005/0178964 A1    Aug. 18, 2005

Related U.S. Application Data

(60) Provisional application No. 60/577,183, filed on Jun. 7, 2004, provisional application No. 60/572,116, filed on May 19, 2004, provisional application No. 60/537,881, filed on Jan. 22, 2004.

(51) Int. Cl.
*H01J 49/28* (2006.01)
*H01J 49/40* (2006.01)

(52) U.S. Cl. .................. 250/288; 250/286; 250/281; 250/282

(58) Field of Classification Search ............... None
See application file for complete search history.

(56) References Cited

U.S. PATENT DOCUMENTS

| | | |
|---|---|---|
| 6,512,224 B1 * | 1/2003 | Miller et al. ............. 250/286 |
| 6,787,765 B1 * | 9/2004 | Guevremont et al. ....... 250/288 |
| 2005/0167587 A1 * | 8/2005 | Guevremont et al. ....... 250/294 |

OTHER PUBLICATIONS

Mason et al., "Transport Properties of Ions in Gases", Wiley, New York, 1988.

* cited by examiner

*Primary Examiner*—Nikita Wells
(74) *Attorney, Agent, or Firm*—Freedman & Associates

(57) ABSTRACT

A method of separating ions includes providing a FAIMS analyzer region for separating ions, and establishing a temperature gradient across the FAIMS analyzer region to controllably affect ion focusing in the FAIMS analyzer region.

27 Claims, 23 Drawing Sheets

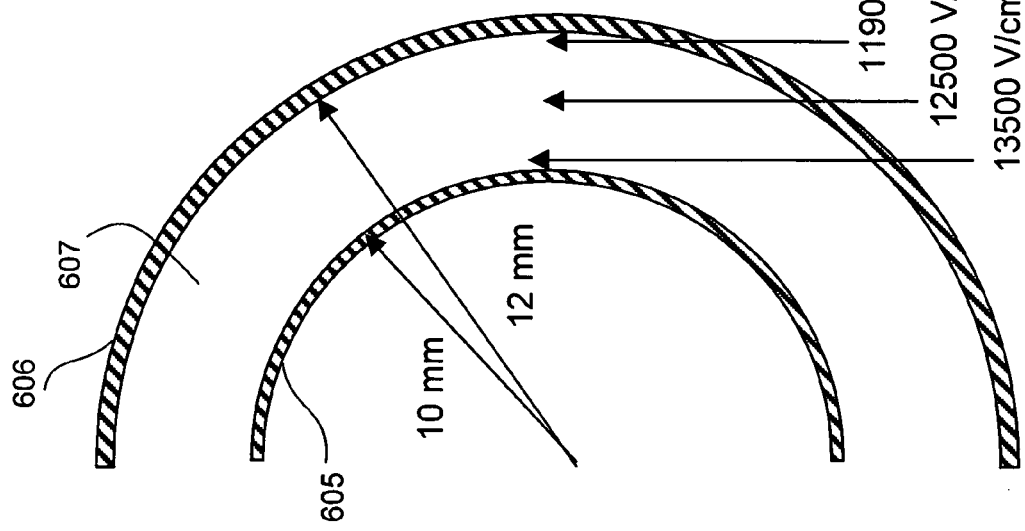
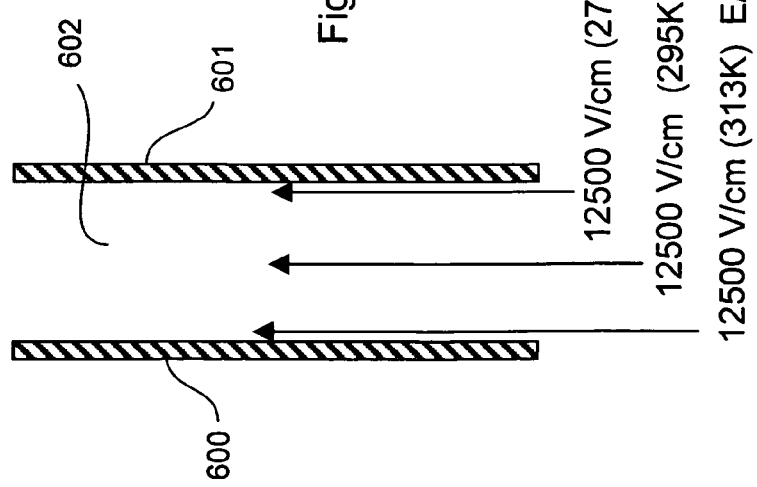
Figure 19b
Figure 19a

APPARATUS AND METHOD FOR ESTABLISHING A TEMPERATURE GRADIENT WITHIN A FAIMS ANALYZER REGION

This application claims benefit from U.S. Provisional application No. 60/537,881 filed Jan. 22, 2004, and from U.S. Provisional application No. 60/572,116 filed May 19, 2004, and from U.S. Provisional application No. 60/577,183 filed Jun. 7, 2004.

FIELD OF THE INVENTION

The instant invention relates generally to High Field Asymmetric Waveform Ion Mobility Spectrometry (FAIMS). More particularly, the instant invention relates to an apparatus for providing control for affecting the temperature in a FAIMS region of a FAIMS system and a method of improving the separation capability of a FAIMS system.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 μs followed by −1000 V for 20 μs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform, an ion moves with a y-axis velocity component given by $V_H = K_H E_H$, where $E_H$ is the applied field, and $K_H$ is the high field ion mobility under operating electric field, pressure and temperature conditions. The distance traveled by the ion during the high voltage portion of the waveform is given by $d_H = V_H t_H = K_H E_H t_H$, where $t_H$ is the time period of the applied high voltage. During the longer duration, opposite polarity, low voltage portion of the asymmetric waveform, the y-axis velocity component of the ion is $V_L = K E_L$, where K is the low field ion mobility under operating pressure and temperature conditions. The distance traveled is $d_L = v_L t_L = K E_L t_L$. Since the asymmetric waveform ensures that $(V_H\ t_H) + (V_L\ t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

In short, a FAIMS device is one which effects ion separation on the basis of the dependence of ion mobility on the electric field strength. In FAIMS the ions are introduced into an analyzer region across which an rf frequency asymmetric waveform is applied such that the ions are alternately subjected to strong electric fields and low electric fields. The field-dependent change in the mobility of the ions causes the ions to drift towards the walls of the analyzer region. Since the dependence of ion mobility on electric field strength is compound specific, this leads to a separation of the different ions, and is referred to as the FAIMS separation or identically, the FAIMS mechanism. In order to transmit an ion of interest through the FAIMS analyzer region, its drift towards the analyzer wall is compensated by applying an appropriate DC voltage for that ion. By varying this compensation voltage, ions are separately transmitted through the FAIMS device.

In an analytical instrument that includes (1) an atmospheric pressure ionization source (for example electrospray ionization (ESI)), (2) an atmospheric pressure gas phase ion separator (for example a high-field asymmetric waveform ion mobility spectrometer (FAIMS)) and (3) an ion detection system (for example a mass spectrometer, MS) it would be advantageous to provide each with independent control for affecting some of the operating conditions including, temperature and operating gas pressure. The ion source, FAIMS, and detection system (mass spectrometer) have significantly different requirements for achieving optimal performance. For example, a mass spectrometer usually operates at room temperature and with a very low pressure or vacuum within the mass spectrometer chamber. The ionization source preferably operates at pressures close to atmospheric, but at elevated temperature so as to assist in desolvation of the ions. The FAIMS electrodes may optimally operate near atmospheric pressure, but at a temperature below ambient.

SUMMARY OF THE INVENTION

It is an object of the instant invention to provide a method and an apparatus that overcomes at least some of the limitations of the prior art.

According to an aspect of the instant invention, there is provided an apparatus for separating ions, comprising: a FAIMS analyzer region defined by a space between a first electrode surface and a second electrode surface, the FAIMS analyzer region having a width defined by a distance between the first electrode surface and the second electrode surface; a gas inlet for introducing a gas into the FAIMS analyzer region; and, a temperature controller in thermal communication with at least one of the first electrode surface, the second electrode surface and the gas for controllably establishing a temperature gradient across the width of the FAIMS analyzer region.

According to another aspect of the instant invention, there is provided a method of separating ions, comprising: providing a FAIMS analyzer region defined by a-space between a first electrode surface and a second electrode surface; and, establishing a temperature gradient across the FAIMS analyzer region between the first electrode surface and the second electrode surface, for affecting ion focusing within the FAIMS analyzer region.

The entire contents of U.S. provisional application No. 60/537,881, 60/572,116 and 60/577,183, which were filed on Jan. 22, 2004, May 19, 2004 and Jun. 7, 2004, respectively, are incorporated herein by reference.

BRIEF DESCRIPTION OF THE DRAWINGS

Exemplary embodiments of the invention will now be described in conjunction with the following drawings, in which similar reference numerals designate similar items:

FIG. 8b is an isometric view of the prior art side-to-side FAIMS that is shown at FIG. 8a;

FIG. 19 compares a) the calculated electric field values for a parallel flat-plate FAIMS with electrodes spaced apart by 0.2 cm assuming a −20 K/mm temperature gradient from left to right in the Figure and with 2500 volts applied between the electrodes and b) calculated electric field values for a cylindrical geometry FAIMS with an inner electrode of radius 0.1 cm and an outer electrode of radius 0.3 cm, assuming no temperature gradient and with 2500 volts applied between the electrodes;

DESCRIPTION OF EMBODIMENTS OF THE INSTANT INVENTION

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Throughout much of the following discussion it is assumed that the FAIMS electrodes are operated at atmospheric pressure, but at a temperature that differs from that of either the ionization source or of the mass spectrometer. Because ion separation in the FAIMS system is susceptible to changes in temperature, it is desirable to have the ability to controllably affect the temperature in the FAIMS region, which includes both heating and cooling. For example, a rise in temperature leads to a decrease in the number density of the gas (N) and therefore the operating electric field (E/N) appears to increase. For some ions this results in a drift of the CV values at which the ions are transmitted through FAIMS. In addition, an elevation in temperature may cause peaks in a CV spectrum to widen due to increased ion diffusion. Under such conditions, two ions that are separated at room temperature may fail to be separated at 100° C., for example. Similarly, two ions that fail to be separated at room temperature may be separated at 10° C. with cooled FAIMS electrodes. Furthermore, the efficiency of transmission of some types of ions through FAIMS is a function of temperature. For instance, some types of ions are subject to thermal dissociation and therefore are more efficiently transmitted through FAIMS in a cool bath gas. Accordingly, it is desirable to be able to controllably affect the temperature of FAIMS to transmit the ions of interest. It is an advantage of at least some embodiments of the instant invention that the temperature of the FAIMS is maintained at a desired operating temperature. It is a further advantage that the temperature of FAIMS is controllably changed from a first desired operating temperature to a second desired operating temperature for different separations. It is an additional advantage that the temperature of FAIMS is independent of the temperature of external instruments, such as for instance the ionization source with which it is in fluid communication.

Figure 1:
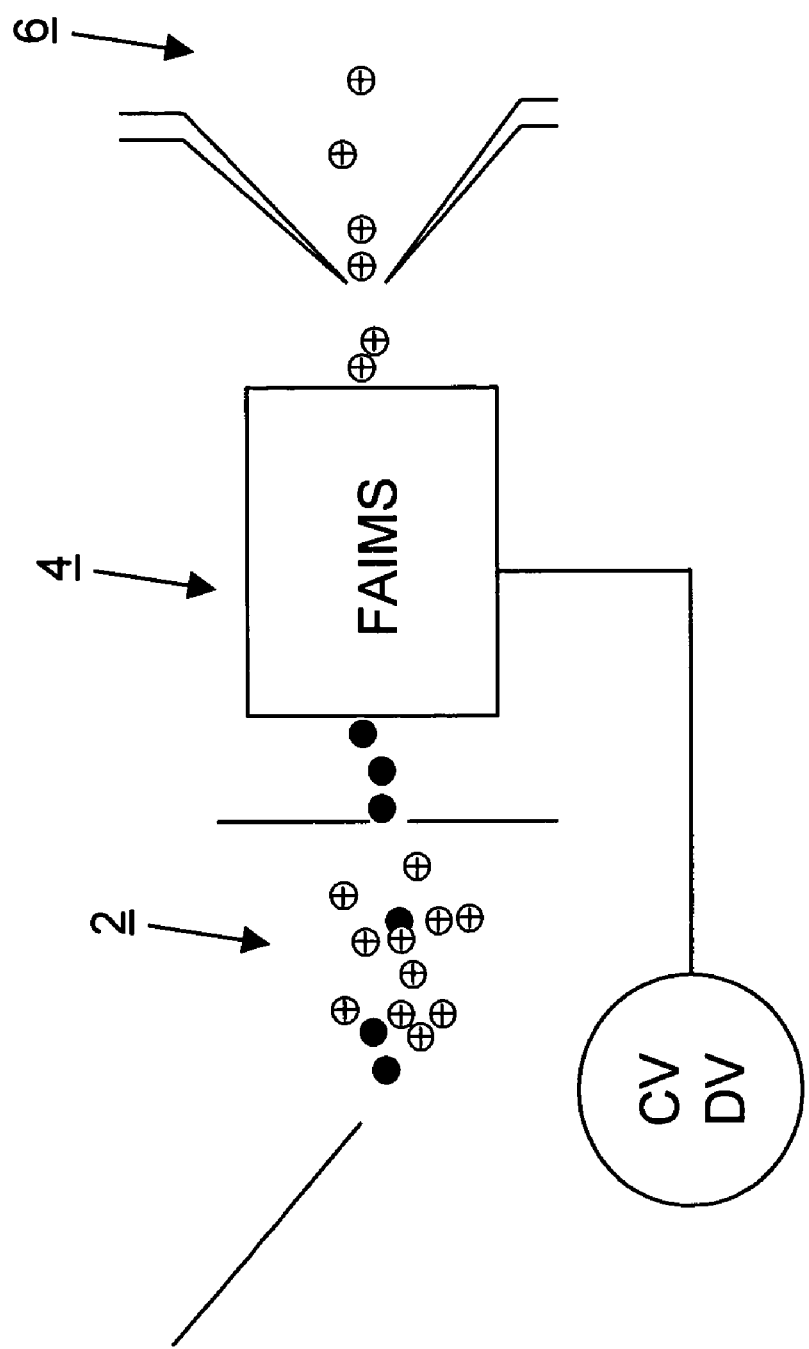
FIG. 1 is a simplified block diagram of an apparatus according to the prior art.

Referring now to FIG. 1, shown is a simplified block diagram of an apparatus according to the prior art. The apparatus that is shown at FIG. 1 is a tandem arrangement including an ion source 2, a FAIMS analyzer 4, and an ion detecting device, such as for example a mass spectrometer 6. The components 2, 4, and 6 are all at about room temperature during operation.

Figure 2:
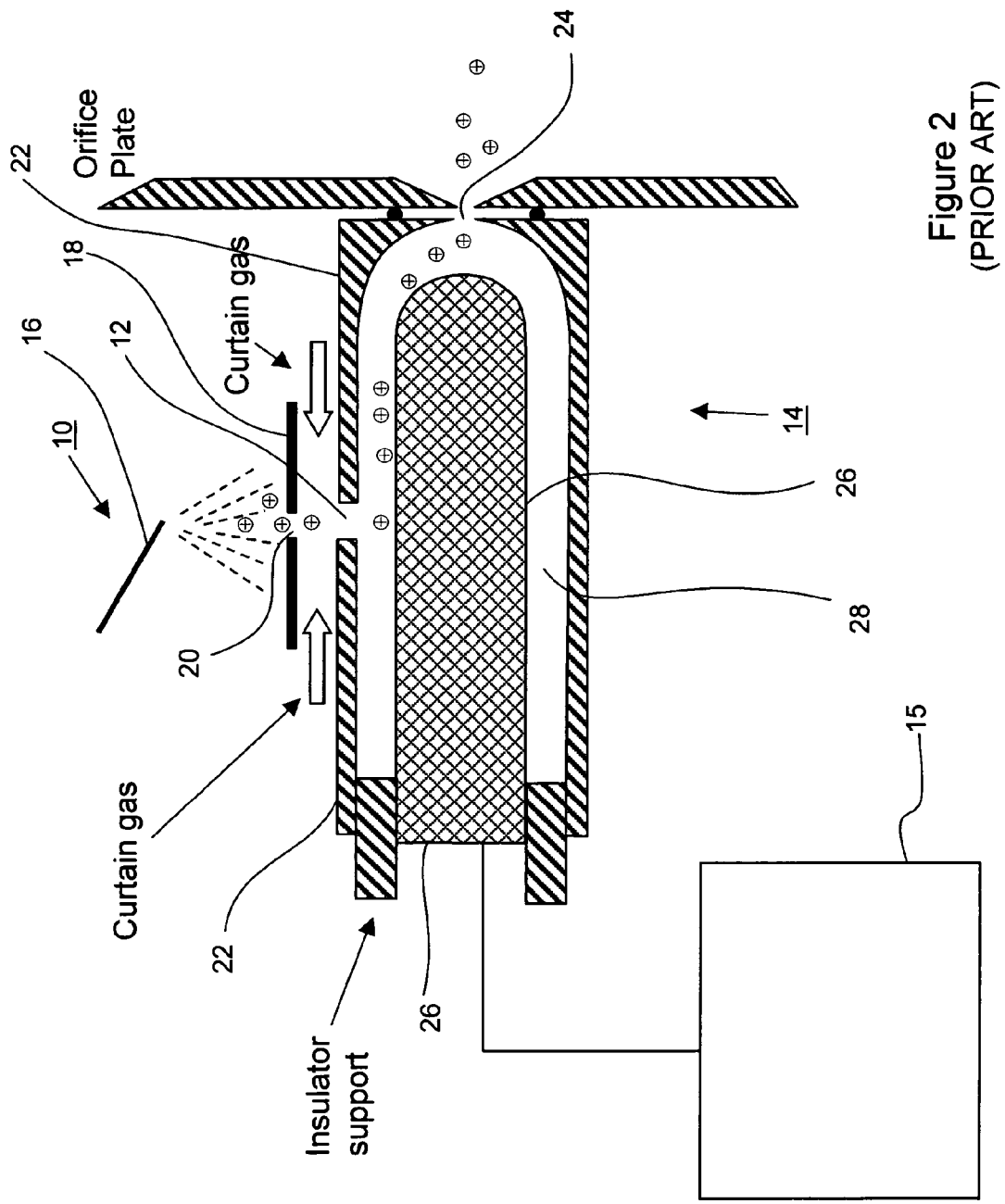
FIG. 2 is a longitudinal cross-sectional view of an apparatus according to the prior art.

Referring now to FIG. 2, shown is a longitudinal cross-sectional view of an apparatus according to the prior art. The apparatus includes an electrospray ionization source 10 that is disposed in fluid communication with an ion inlet 12 of a FAIMS 14. In FIG. 2, the ions are formed near the tip of an electrospray needle 16 and drift (under the influence of an electrical field gradient) toward a curtain plate 18. A curtain gas, which is introduced below the curtain plate 18, divides into two flows, one of which exits through an aperture 20 in the curtain plate 18 so as to substantially prevent neutrals and droplets from entering the curtain plate aperture 20. Ions are driven against this flow of gas by a voltage gradient that is established between the electrospray needle 16 and the curtain plate 18. A field that is generated between the curtain plate 18 and a FAIMS outer electrode 22 pushes ions that pass through the aperture 20 in the curtain plate 18 toward the ion inlet 12 of FAIMS 14. A portion of the curtain gas flows into the ion inlet 12 and carries the ions along the length of the FAIMS electrodes to an ion exit 24, and into a not illustrated mass spectrometer.

In this example, a high voltage asymmetric waveform is applied, using a suitable asymmetric waveform generator 15, to an inner electrode 26 of FAIMS 14, so as to produce an electric field that causes ions within an annular space between the inner electrode 26 and the outer electrode 22, which annular space is referred to as the analyzer region 28, to oscillate between the inner electrode 26 and the outer electrode 22. The waveform is generated in such a way to cause the ions to move in a first direction in a strong field for a short period of time, followed by motion in the other direction in a weaker field for a relatively longer period of time. Absent any change in ion mobility between the high field and low field portions of this applied asymmetric waveform, after each cycle of the waveform the ion returns to its original position relative to the surface of the electrodes (without consideration of diffusion or ion-ion repulsion). In practice however, the mobility of many ions is different in strong and weak electric fields and for these ions the position after one cycle of the waveform is not identical to the starting position of the ion relative to the electrode surfaces. This gives rise to the separation of ions as the net displacement of the ion after one cycle of the waveform is compound dependent. This is sometimes referred to as the FAIMS mechanism of separation. A second, direct current voltage, which is referred to as the compensation voltage (CV), is applied to eliminate or compensate for this change of position. If the compensation voltage is of a magnitude that eliminates or compensates for the change of position that would occur absent the compensation voltage, then the ion returns to about the same relative location after each cycle of the waveform. Thus the ion does not migrate towards one or the other of the electrodes, and is therefore transmitted through FAIMS 14 under the influence of a carrier gas flow, for example. Other ions, for which the compensation voltage is too high or too low to compensate for the net displacement of the ion relative to the electrodes during one cycle of the waveform, drift toward an electrode and are unable to pass through FAIMS 14. Thus by selecting the appropriate CV, an ion of interest is transmitted through the FAIMS analyzer.

Figure 3:
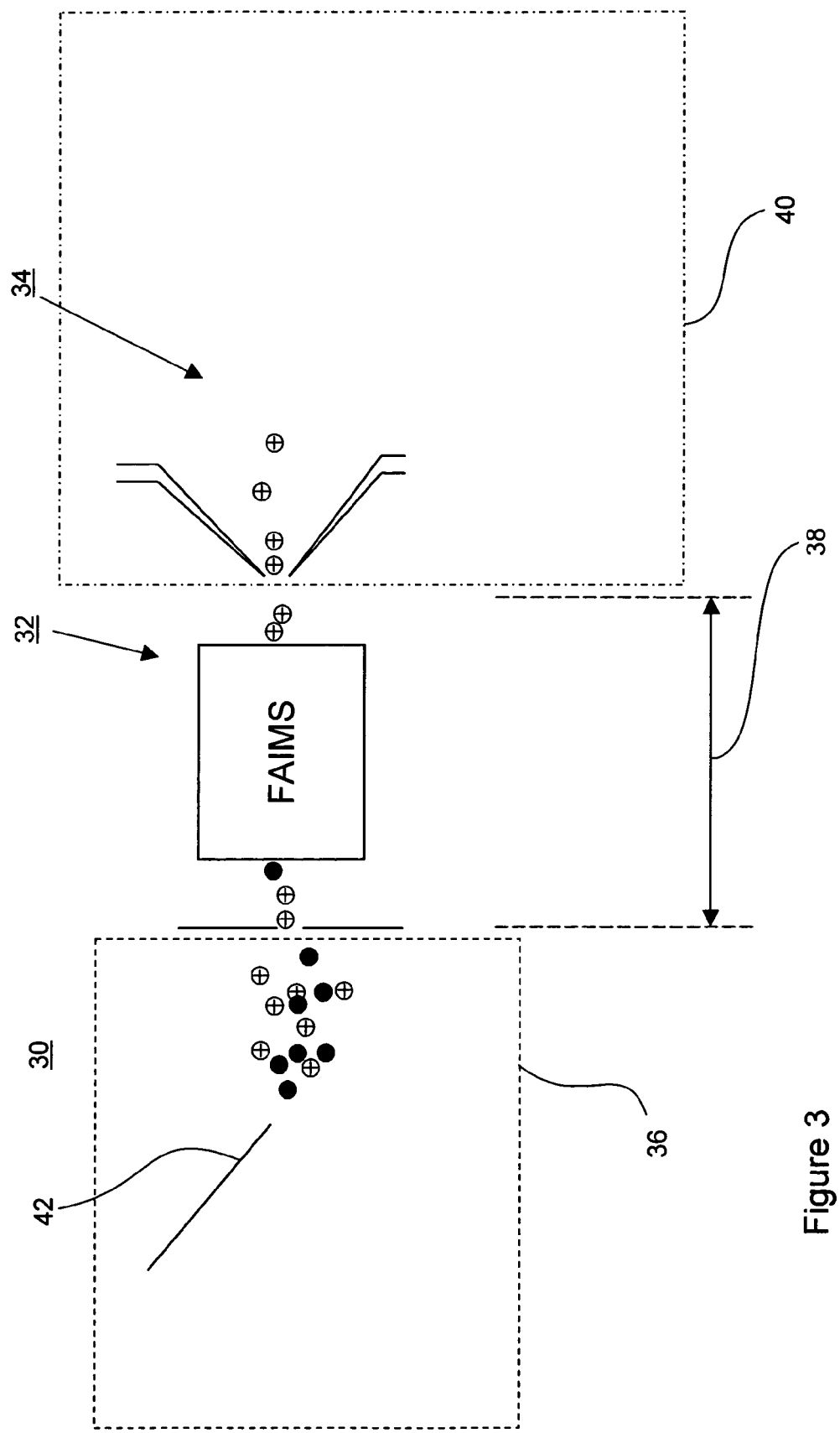
FIG. 3 is a simplified block diagram of an apparatus according to an embodiment of the instant invention.

Referring now to FIG. 3, shown is a simplified block diagram of an apparatus according to an embodiment of the instant invention. In particular, FIG. 3 illustrates a tandem arrangement including an ion source 30, a FAIMS device 32, and an ion detector 34 such as for example a mass spectrometer. Preferably, the apparatus of FIG. 3 supports independent control for affecting the temperature and/or pressure of an ion source region 36, a FAIMS region 38, and an ion detection region 40 such that the temperature and/or pressure of any one region is controllably adjustable and is independent of the temperature and/or pressure of the other regions. Of course, other arrangements are envisaged where not every one of the ion source region 36, the FAIMS region 38, and the ion detection region 40 is provided with means for controllably affecting the temperature and/or pressure thereof. While the control of temperature is emphasized throughout this document, it is to be understood that operation at gas pressures higher than and lower than atmospheric pressure is also envisaged. For example the ion source 30 is operated at twice atmospheric pressure provided an appropriate chamber (not shown) surrounds the ion source region 36, and the FAIMS analyzer 32 is operated at 0.3 of an atmosphere assuming an appropriate chamber (not shown) surrounding the FAIMS region 38 and appropriate apertures (not shown) separating the ion source region 36 and the FAIMS region 38 are provided. Of course, any mention of specific operating pressures and/or temperatures is given by way of non-limiting example only. Similarly, any FAIMS analyzer of a different electrode geometry is optionally used with the instant invention including as some non-limiting examples: concentric cylinder geometry electrodes with or without a domed inner electrode; parallel plate geometry electrodes; concentric cylinder geometry electrodes operating in a side-to-side mode; spherical electrodes; quadrupolar electrodes; etc.

Typically, the ion source 30 that is shown at FIG. 3 includes provision for affecting the temperature, such as by heating, of either the ionization process or the not illustrated chamber that surrounds the source region 36. Using electrospray ionization as a non-limiting example of an ion source for discussion purposes, the most common type of heat addition used in this ionization technique is through the application of a nebulizer gas in a concentric arrangement around the electrospray needle 42, where the nebulizer gas is pre-heated to promote desolvation of the small droplets formed by electrospray ionization. Alternatively, a stream of hot gas is directed toward the plume of ions/droplets coming from electrospray needle 42. Optionally, the not illustrated chamber that houses the ion source 30 is operated at elevated temperature.

Figure 4:
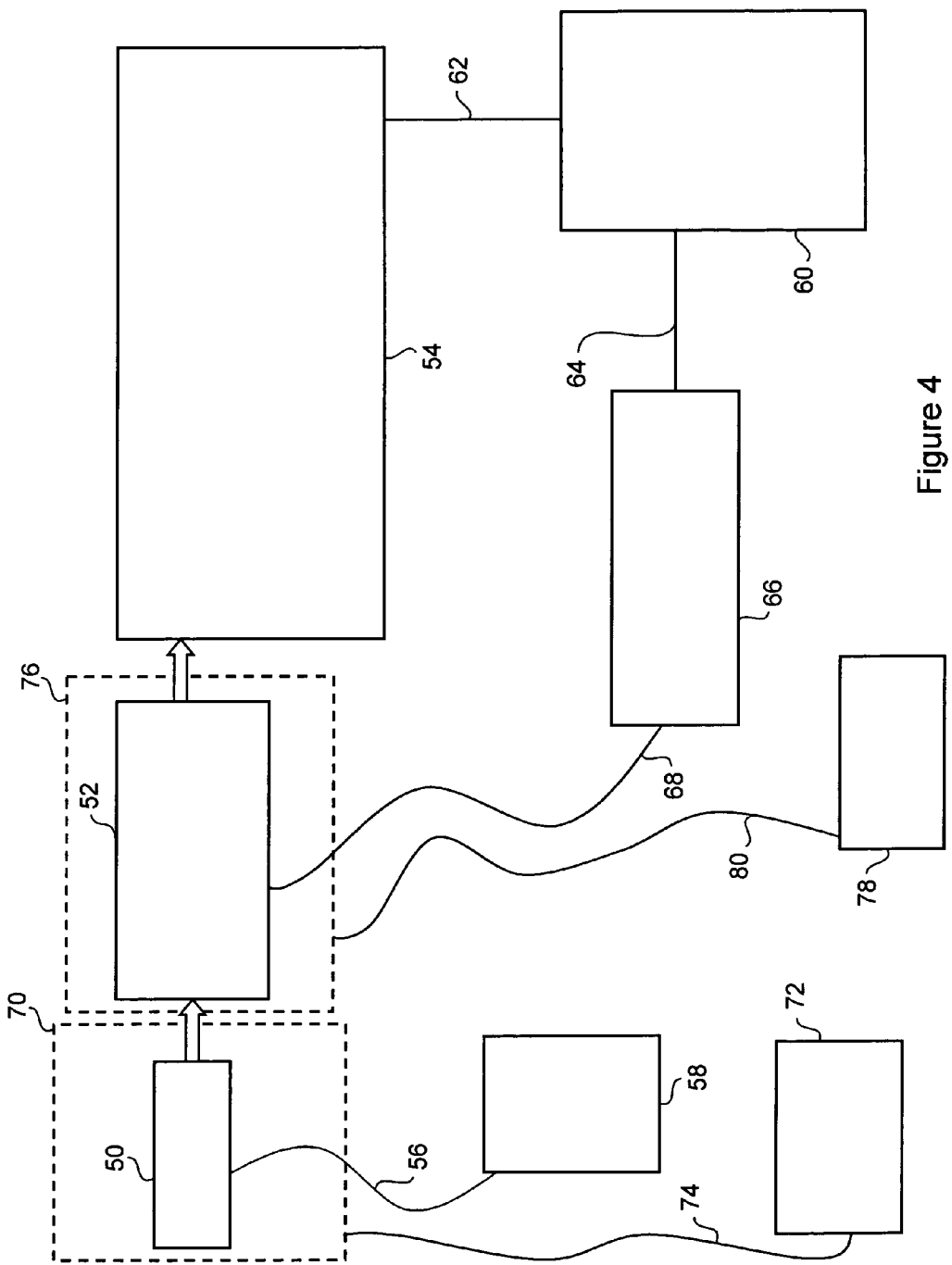
FIG. 4 is a simplified block diagram of another apparatus according to an embodiment of the instant invention.

Referring now to FIG. 4, shown is a block diagram of another apparatus according to an embodiment of the instant invention. An ionization source 50 is provided. Ions produced at the ionization source 50 are separated in a FAIMS analyzer 52. The subset of ions that passes through (i.e. exits from) the FAIMS analyzer 52 are introduced into an ion detecting device, which in this non-limiting example is a mass spectrometer 54. The ions that pass through the FAIMS analyzer 52 are further separated, according to mass-to-charge ratio (m/z), and/or detected within the vacuum chamber of the mass spectrometer 54. According to the present embodiment, sample solution optionally is delivered to the ionization source 50 via a capillary tube 56 connected to a liquid chromatography (LC) system 58. Optionally the LC system 58 is a high pressure LC (HPLC) or another condensed phase separation system such as capillary electrophoresis. Data from the mass spectrometer 54 is carried to a computer or other suitable processor 60 via a coupling 62. The processor 60 is used to process the data and is optionally used to control the operation of one or more components of the system. For example, information pertaining to the experimental setup is delivered via a coupling 64 to a power supply 66 that in turn is connected via coupling 68 to the FAIMS analyzer 52. Optionally, experimental information is also exchanged via a not-shown coupling between the processor 60 and the HPLC system 58. The apparatus shown at FIG. 4 illustrates some of the features of a complex, processor controlled analysis system that includes atmospheric pressure ionization and FAIMS.

Referring still to FIG. 4, the apparatus includes a temperature controller for controlling the temperature of the ionization source 50 and of the FAIMS analyzer 52. To this end, the ionization source 50 is disposed inside a containment system 70 that isolates the source from its surroundings and from other components of the apparatus. Optionally, a pressure controller is provided also. A controller 72 is in communication with the ionization source 50 via coupling 74 for controlling the temperature and/or pressure of the ionization source 50. For example, if high liquid sample flow rates are required, then the containment system 70 is held at a temperature that is above room temperature to assist in desolvation of the ions. In this example the containment system 70 is also held at a pressure that is above atmospheric pressure in order to simplify transmission of ions out of the source 50 to the FAIMS analyzer 52. The FAIMS analyzer 52 is also held in an isolation chamber 76 suitable for control of temperature and pressure. The containment system 70 and the isolation chamber 76 optionally have a common wall including a port for supporting ion transmission therebetween. Controller 78 and connection 80 are used to control the temperature and pressure of the isolation chamber 76 that contains the FAIMS analyzer 52.

In this example the FAIMS analyzer 52 is held at a pressure higher than atmospheric pressure, and at a temperature below room temperature in order to maximize the transmission efficiency and the ion separation resolution efficiency.

The ionization source 50 and the FAIMS analyzer 52 are operable independently over a wide range of temperature and pressure values. However, the requirements for the operating temperature of the ion source and the operating temperature of FAIMS may differ, and therefore it is preferable that one is thermally isolated from the other. For instance, the isolation chamber 76 includes a housing having an insulating layer for thermally isolating the FAIMS analyzer 52 from a region external to the housing.

Figure 5:
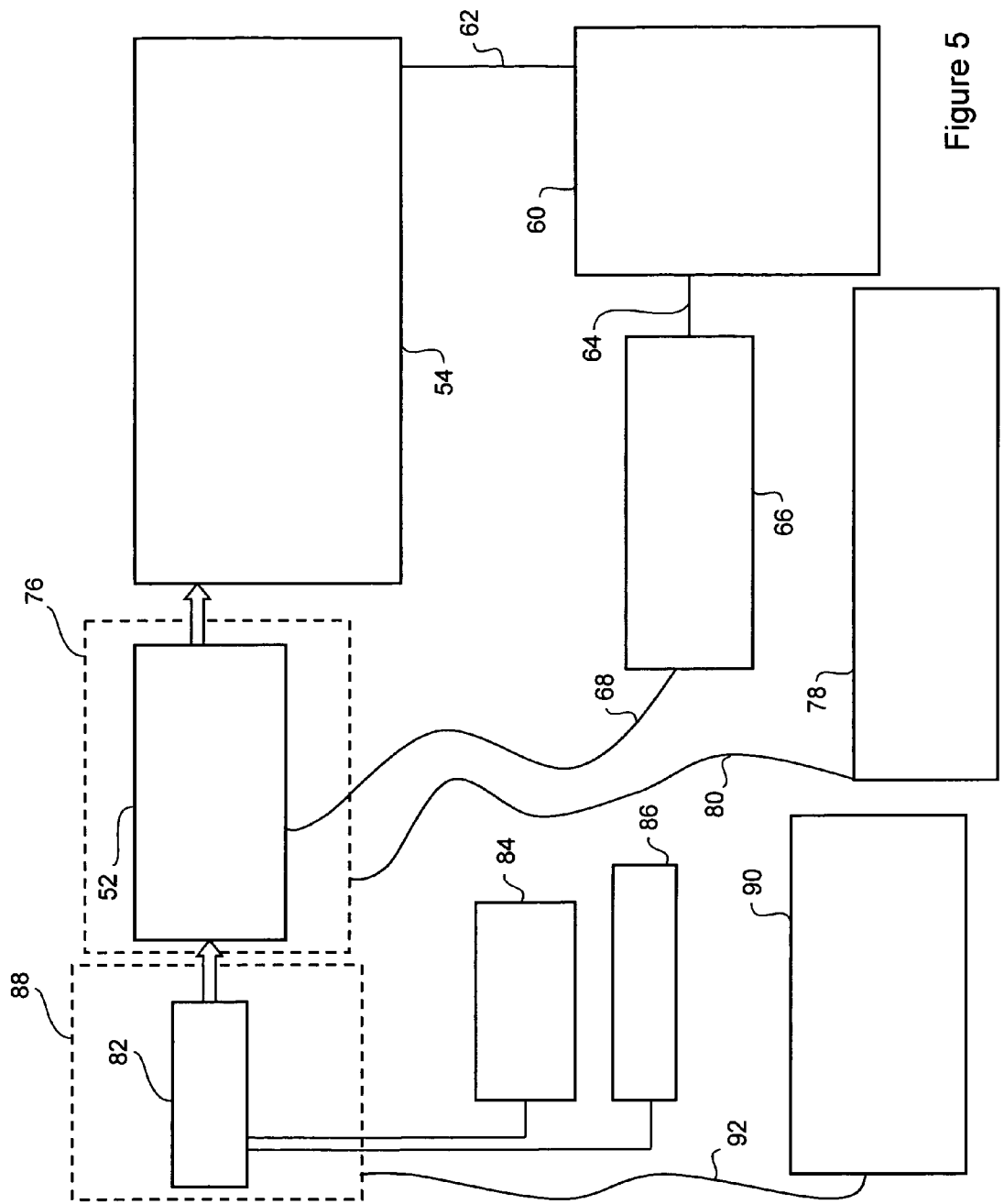
FIG. 5 is a simplified block diagram of yet another apparatus according to an embodiment of the instant invention.

FIG. 5 illustrates a system similar to the one that is shown at FIG. 4, except that the atmospheric pressure ionization source is a MALDI source 82. Of course, this non-limiting example is intended to encompass other laser ionization techniques. Many of the similarly numbered components that are shown in FIG. 5 have the same meaning as those that are shown in FIG. 4. The MALDI source 82 includes a sample support platform (not shown) that is controlled by electronics unit 84. The MALDI source 82 also includes a laser (not shown) that is controlled by the laser power supply 86. The MALDI source 82 is enclosed in a temperature and pressure controlled chamber 88 that is controlled by controller 90 via control link 92 between chamber 88 and controller 90. The MALDI source is operable over a wide range of pressure and temperature conditions, and in many cases is considered a low-pressure ionization source. FAIMS is operable at low pressure, and therefore the chamber 88 containing MALDI, and the isolation chamber 76 that contains the FAIMS analyzer 52 are both operable at pressures below atmospheric pressure. Optionally, chamber 88 and chamber 76 share a common wall including a port for supporting the transmission of the ions therebetween.

Figure 6:
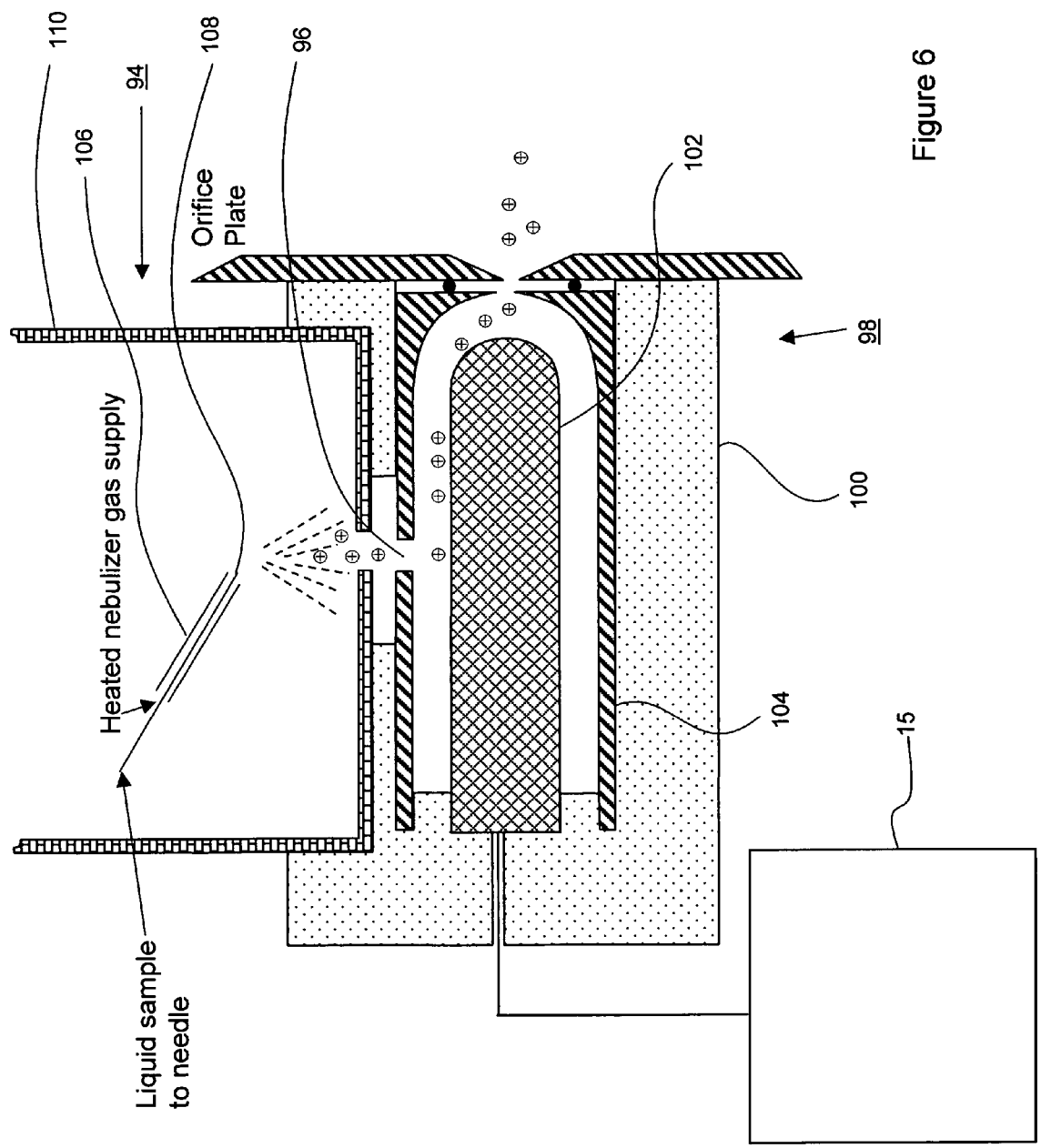
FIG. 6 is a longitudinal cross-sectional view of an apparatus according to an embodiment of the instant invention and including a heated electrospray ionization source that is in fluid communication with an ion inlet of a FAIMS.

Referring now to FIG. 6, shown is a longitudinal cross-sectional view of a heated electrospray ionization source 94 in fluid communication with an ion inlet 96 of a FAIMS 98. The FAIMS 98 is mounted in and supported by an electrically insulating block 100 made of a material with high dielectric strength to prevent electrical discharge. Some non-limiting examples of suitable materials for use as the electrically insulating block 100 include Teflon™, and PEEK. According to FIG. 6, the electrically insulating block 100 supports the inner electrode 102 and the outer electrode 104 in a spaced-apart arrangement. For simplification, not all electrical connections are shown, and the details of the curtain gas delivery, including a curtain plate and a passageway for providing the curtain gas, are not shown.

In the specific and non-limiting example of FIG. 6, the FAIMS 98 lacks a temperature controller. However, the ionization source 94 is provided with a temperature controller in the form of a heated nebulizer gas supply delivered through tube 106 in concentric arrangement around the electrospray needle 108 in order to assist in formation of small droplets, and in order to assist in desolvating the ions. In this specific and non-limiting case, the nebulizer gas is pre-heated. The electrospray needle 108 is enclosed in a chamber 110 that supports control of the bath gas composition, temperature and gas pressure. Without control of the temperature of FAIMS 98, the FAIMS electrodes 102 and 104 and the electrically insulating block 100 gradually change temperature during operation, and eventually equilibrate to some unspecified temperature. It is a disadvantage of this approach that the FAIMS 98 cannot be used during the time required to reach temperature equilibration. It is also a disadvantage that the final temperature of the FAIMS 98 is unknown, and is not controllable. The final temperature depends on the heat that is transferred from the heated electrospray ionization source 94, the heat that is transferred to and from the not illustrated ion detector adjacent to the FAIMS ion outlet interface, and on the thermal properties of the FAIMS 98.

Figure 7:
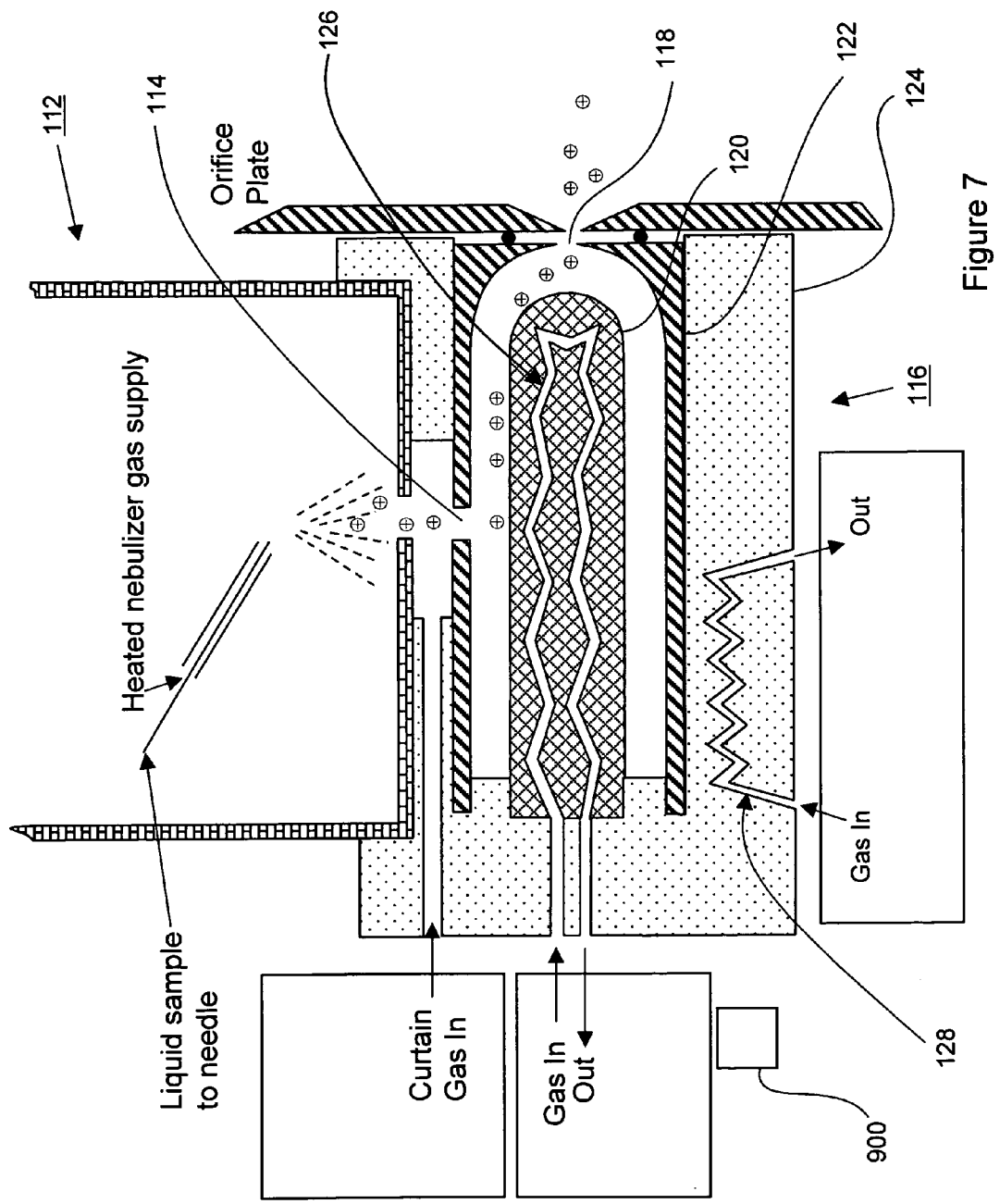
FIG. 7 is a longitudinal cross-sectional view of an apparatus according to an embodiment of the instant invention and including a heated electrospray ionization source that is in fluid communication with an ion inlet of a FAIMS that is equipped with a heating/cooling system.

Referring now to FIG. 7, shown is a longitudinal cross-sectional view of a heated electrospray ionization source 112 in fluid communication with an ion inlet 114 of a FAIMS 116 including a temperature controller according to an embodiment of the instant invention. For simplification, not all electrical connections are shown. In this specific and non-limiting example, the FAIMS 116 includes a temperature controller. The FAIMS 116 in this non-limiting example is a cylindrical electrode geometry FAIMS analyzer with a domed inner electrode. Of course, this non-limiting example is intended to encompass other electrode geometries of FAIMS. It is preferred, but not essential, that the gas temperature at the source of the curtain gas flow be adjusted so that the temperature of the stream of curtain gas that transports the ions into and through FAIMS 116 remains approximately constant, at least to within a known tolerance limit, between the ion inlet 114 and an ion outlet 118. Changes in temperature of the gas while the ions are being transported through FAIMS 116 results in a loss of the balance between the asymmetric waveform and compensation voltage that is needed to transport a particular ion. Consider one specific and non-limiting example. If ions enter FAIMS 116 and the temperature of the gas and the voltages are exactly balanced to transmit an ion of interest, the ion of interest drifts parallel to the surfaces of the inner electrode 120 and the outer electrode 122, being carried by the gas (superimposed with the oscillation motion caused by the waveform) to the ion outlet 118. If the temperature of the gas begins to change, for example because the electrodes 120 and 122 are warmer than the gas entering FAIMS 116, then the balanced condition may no longer exist and the ions of interest that were being transported begin to drift towards one of the electrodes 120 or 122, and are lost by collision with the electrode 120 or 122. It is advantageous, from the point of view of efficiency of ion transmission, that the conditions be approximately constant during the passage of the ion through FAIMS 116. To this end, a temperature sensor 900 is provided for sensing a temperature that is based upon a temperature within a portion of the FAIMS 116, and for providing an output signal in dependence upon the sensed temperature. The temperature controller, which is in communication with the temperature sensor, receives the output signal and controllably affects the temperature within the portion of the FAIMS 116 in dependence thereon. Temperature control includes any one of adding heat, removing heat or making no change in dependence upon a difference between or a sameness of the sensed temperature and the desired temperature. Non-limiting examples of a temperature sensor include thermometers, thermocouples and optical temperature measuring devices such as a fluoroptic probe.

In some cases, a change in conditions during passage of an ion through FAIMS 116 promotes separation of ions with similar properties, and hence enhances the resolution of the device. The ions are exposed to conditions that change while traveling along the FAIMS analyzer region if, for example, there is a temperature change in the gas between the ion inlet and the ion outlet of FAIMS. Creating a temperature difference between a first zone of the analyzer region, for instance the beginning of the ion pathway between the FAIMS electrodes and a second zone of the analyzer region, for instance, further along the length of the ion pathway is difficult to control accurately, but is an option encompassed by at least some of the embodiments of the instant invention. In practice, simpler opportunities to promote separation arise through a change in electrode geometry (e.g. a dome at the end of the cylindrical inner electrode constitutes a change in separation conditions). Other possibilities include a change of electrode spacing, or a change of applied voltages that the ion experiences during its passage through FAIMS. These changes, if controlled, maintain transmission efficiency, while enhancing the separation resolution.

Control of the curtain gas temperature is beneficial, as discussed above. It has also been found to be beneficial to control the temperature of the inner electrode 120, the outer electrode 122, and the electrically insulating block 124 that supports the electrodes. Still referring to FIG. 7, the system includes a temperature controller in the form of a suitable structure for introducing a plurality of controlled-temperature flows of a heat-exchange fluid. The heat-exchange fluid preferably is gas phase, but optionally a liquid phase heat-exchange fluid is used. In the interest of brevity, and for non-limiting discussion purposes only, a gas-phase heat-exchange fluid is discussed, however it is to be clearly understood that a liquid-phase heat-exchange fluid is also envisaged for use with the various embodiments of the instant invention. Because of the high voltage of the asymmetric waveform applied to one of the FAIMS electrodes, it is desirable that the heat-exchange fluid is an electrically insulating substance and is also capable of resisting electrical discharge. Because of the high voltage of the asymmetric waveform applied to one of the FAIMS electrodes, the temperature sensor is selected so as not to interfere with the ability of the waveform generator to provide the required high voltage asymmetric waveform or such that its ability to function is not susceptible to the electric field.

FIG. 7 illustrates the use of a temperature controller in the form of a flow of a heat-exchange fluid (preferably gas phase but optionally liquid phase), which passes through a heat-exchange passage 126 within some portion of the inner electrode 120, and a flow of a heat-exchange fluid (preferably gas phase but optionally liquid phase) that passes through a heat-exchange passage 128 within some portion of the electrically insulating block 124, so as to controllably add heat to or remove heat from the FAIMS system. Although not shown in FIG. 7, the temperature controller optionally includes a flow of a heat-exchange fluid (preferably gas phase but optionally liquid phase) through a not illustrated heat-exchange passage within a portion of the outer electrode 122. Each flow of a heat-exchange fluid is adjusted to a pre-selected temperature prior to delivery to the corresponding heat exchange area, as shown in FIG. 7. The temperature of each heat-exchange fluid is adjusted by monitoring the temperatures of each FAIMS component using a temperature sensor, for example optical thermal sensors, which provide feedback relating to the temperature. Each heat-exchange fluid temperature is adjusted to maintain the FAIMS component at a constant temperature, and to support transmission of the ions through FAIMS under temperature conditions that are considered optimal for the ion separation being performed. For example the electrode set is cooled (instead of heated) to permit transmission of a thermally labile species.

Of course, in practice, the heat-exchange fluid is any suitable gas or liquid. Optionally, different heat-exchange fluids are provided to the different heat-exchange passages 126, 128, etc. Furthermore, the temperature sensor optionally is selected from known temperature sensors including but not limited to a thermometer, a thermocouple, and optical temperature sensing devices, such as a fluoroptic probe.

The system in FIG. 7 also ensures that the temperature is stabilized quickly after a new temperature condition is selected. This minimizes the time that is lost during equilibration.

Numerous temperature controllers for controllably affecting temperature are feasible for use with the embodiments of the instant invention. However, not all of these temperature controllers are equally practical for use with a FAIMS system. For example, the inner electrode 120 of FAIMS 116 in FIG. 7 operates at high voltages that are applied by the not illustrated asymmetric waveform generator; therefore, preferably the selected heat-exchange fluid in heat exchange passage 126 is a sufficiently good insulating medium such that electrical leakage current through the heat exchange-fluid does not exceed the current-producing capability of the asymmetric waveform generator and, in this way, does not degrade the performance of the not illustrated high voltage asymmetric waveform generator. In addition, the heat-exchange fluid must resist electric discharge. In another example where the design of the waveform generator is such that the application of the waveform on the inner electrode 120 makes the electrodes a part of a delicately balanced electronic inductor-capacitor (LC) tuned circuit, the heating/cooling process must not upset this balance. For instance, the use of a temperature controller in the form of an electronic heater cartridge within the inner electrode 120 is not practical, nor desirable, because of the excess distributed capacitance added, and the additional opportunities for electric discharge which originate from the electrical wires and external power supply that are necessary to operate the heater cartridges. These arguments also apply to temperature controllers in the form of electronic cooling cartridges. That said, a temperature controller in the form of electronic heater cartridges and electronic cooling cartridges certainly are viable options for affecting the temperature of the outer electrode 122 and/or the electrically insulating block 124 that supports the FAIMS electrodes. In this example, the use of a thermocouple as the temperature sensor associated with the inner electrode is not desirable for the same reasons discussed above relating to the additional opportunities for electric discharge which originates from the additional wiring needed for the thermocouple.

Optionally, a temperature controller including a liquid-phase coolant/heating fluid is used, although a leak of the fluid near the opening into the vacuum chamber of the not illustrated mass spectrometer may damage the instrument, if a leak of water (for example) permits liquid water to enter the vacuum chamber of the not illustrated mass spectrometer. Similarly, a leak of a liquid coolant into FAIMS may have serious consequences including shorting of the waveform generator power supply. In contrast, leaks of a gaseous phase heat/cooling fluid into either the mass spectrometer or FAIMS are expected to have less dire consequences. A leak of gas-phase heat-exchange fluid into FAIMS, although inconvenient because it is likely to affect the separation of ions, is not expected to destroy the instrument.

Finally, preferably the heating/cooling capacity of the selected heat-exchange fluid is high enough to re-adjust the temperature of the FAIMS system after being set to a new temperature, at a rate that is useful under typical operating conditions, and to achieve a desired temperature for a particular application. Gases typically have much lower heat capacities than do liquid-phase mediums. The flow rate and the temperatures of each fluid delivered to FAIMS are typically selected to achieve thermal stabilization within about 15 minutes. Since the ion source 112 takes time to stabilize after being set to operate at a new temperature, it is advantageous to have FAIMS also stabilize within the same time period. Preferably, the temperature controller maintains the temperature of the FAIMS within a pre-determined range of values about the desired temperature, even under changing temperature conditions external to the FAIMS. To this end, the temperature sensor 900 is provided for sensing a temperature that is based upon a temperature within a FAIMS, and for providing an output signal in dependence upon the sensed temperature. The temperature controller is in communication with the temperature sensor and controllably affects the temperature within the FAIMS in response to the output signal of the temperature sensor. By way of non-limiting examples, the temperature sensor may use physical, chemical, electrical or optical means or a combination thereof to sense a temperature and provide an output signal in dependence upon the sensed temperature.

Prior to evaluation with prototypes, it was unknown whether gas streams, as described above, would be suitable for controllably affecting temperature according to the embodiments of the instant invention. Only after experimental testing was it determined that gases were suitable for this purpose. In test systems, the electrodes were operated at temperatures up to 180° C. and cooled to temperatures approaching 0° C. In one non-limiting example, nitrogen gas was used as the heat exchange fluid. In particular, for cooling purposes, nitrogen gas was provided from a top portion of a dewer flask containing a supply of liquid nitrogen, and for heating purposes the nitrogen gas was passed through heater cartridges external to the FAIMS prior to being passed through the heat exchanger regions of the FAIMS electrode set. Using nitrogen gas as described above supported operation of the FAIMS electrode set at temperatures between 10° C. and 120° C.

It should be noted that temperatures below 0° C. are also envisaged for certain applications, however, additional precautions are required in order to avoid condensation and/or freezing along internal and/or external surfaces of the FAIMS components. For instance, preferably the internal and external surfaces of the FAIMS are maintained in contact with dried, ultra-pure gases. Similarly, temperatures well in excess of 180° C. are also envisaged, but with judicious selection of the materials that are used to fabricate the components of the FAIMS. For instance, one possible material is ceramics.

Since the FAIMS electrodes are optionally fabricated in many ways, including but not limited to, concentric cylinders, two parallel plates (flat or curved), multiple stacked parallel plates (flat or curved), spherical and cylindrical electrodes terminating in a hemisphere (such as for instance the domed electrodes of FIG. 2), one additional example of a system for heating/cooling of FAIMS electrodes is considered here.

Figure 8A:
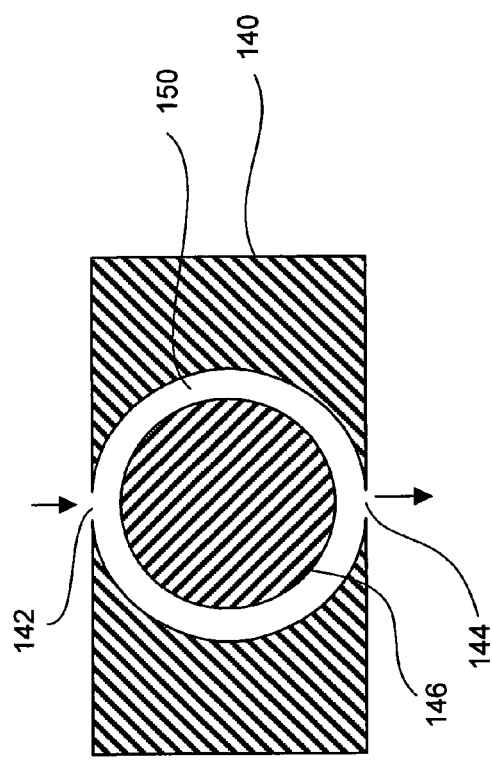
FIG. 8a is an end view of a prior art side-to-side FAIMS having an outer electrode with a rectangular-shaped outer surface.
Figure 8B:
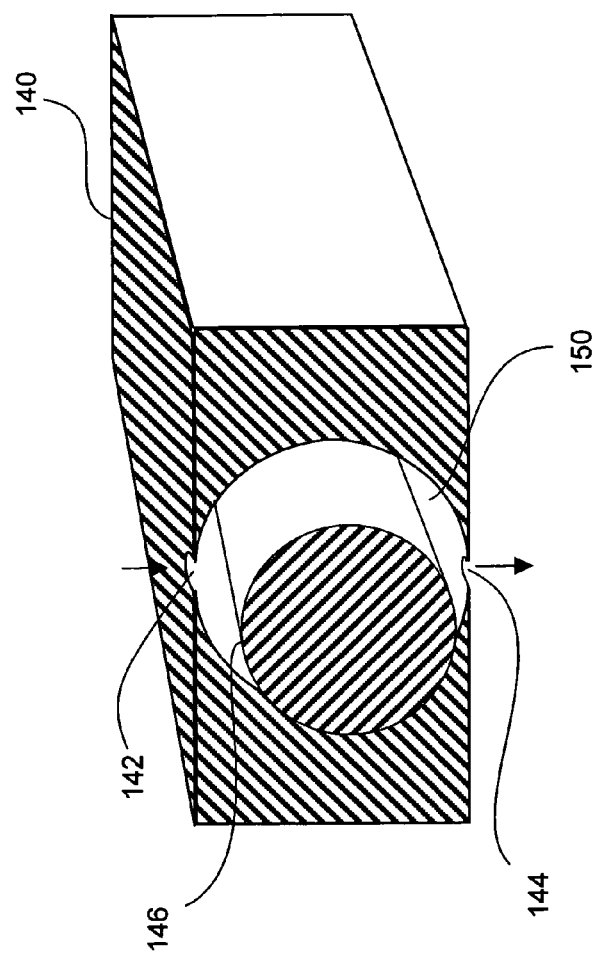

Referring now to FIGS. 8a–8b, shown is a side-to-side FAIMS device including an outer electrode 140 that is a rectangular solid having openings in the top and bottom (opposite surfaces) thereof for defining the ion inlet 142 and the ion outlet 144, respectively. This is known as the side-to-side FAIMS geometry, as described for example by Guevremont and Purves in WO 01/69216, filed on Mar. 14, 2001 and which is incorporated herein by reference, by Guevremont et al. in WO 03/067236, filed on Feb. 07, 2003 and which is incorporated herein by reference, and by Guevremont et al. in WO 03/067243 filed on Feb. 07, 2003 and which is incorporated herein by reference. Typically the inner electrode 146 extends beyond the end of the outer electrode 140 and thus fits into a not illustrated electrically insulating block fixed to the ends of the rectangular outer electrode 140 (details not shown here). Other ways of securing the inner electrode 146 in the not illustrated electrically insulating block may also be envisaged. In all the embodiments described above, the inner electrode 146 and the outer electrode 140 are optionally made of an electrically conductive material, or one or both of the inner electrode 146 and the outer electrode 140 are made of nonconductive material having a conductive material applied to the outer surface in the case of the inner electrode 146, and to the inner surface in the case of the outer electrode 140.

In the side-to-side FAIMS, a stream of ions that enters the ion inlet 142 divides approximately equally into two separate streams, each of which passes along an annular space 150 between the inner electrode 146 and outer electrode 140, on opposite sides of the inner electrode 146. Upon the application of an rf asymmetric potential waveform to one of the electrodes, the annular space 150 acts as the analyzer region where FAIMS separation occurs.

Figure 9:
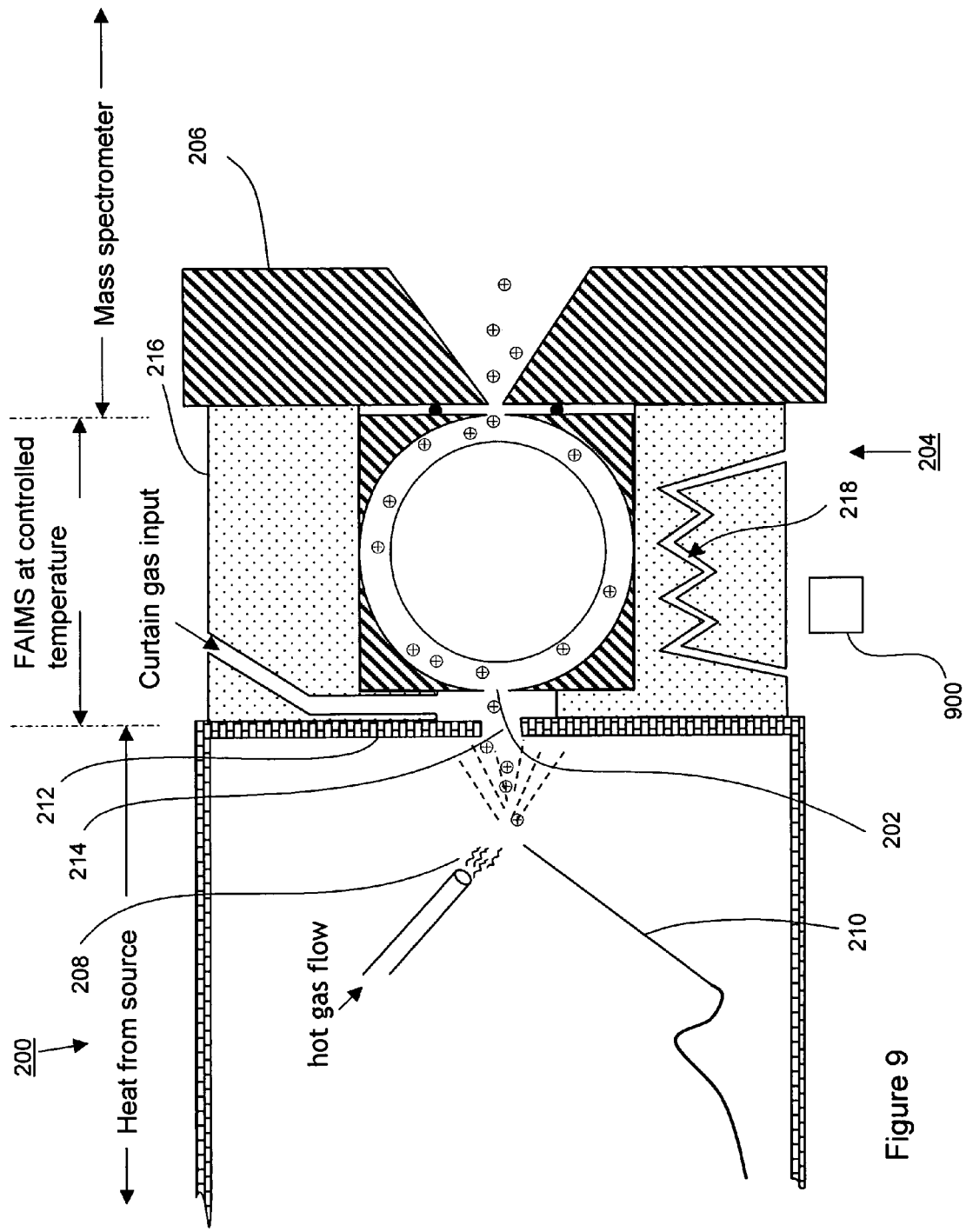
FIG. 9 is a longitudinal cross-sectional view of an apparatus according to an embodiment of the instant invention and including heated electrospray ionization source that is in fluid communication with an ion inlet of a side-to-side FAIMS that is supported by an insulating block including a heat exchange passage.

Referring now to FIG. 9, shown is a cross sectional view of a heated electrospray ionization source 200 in fluid communication with an ion inlet 202 of a side-to-side FAIMS 204 including a temperature controller according to an embodiment of the instant invention. The side-to-side FAIMS device 204 is mounted between the heated electrospray ionization source 200 and the front plate 206 of the vacuum chamber of a not illustrated mass spectrometer. The heated electrospray ionization source 200 shown at FIG. 9 uses a hot gas jet 208 to improve the rate of desolvation of the electrically charged droplets produced at the electrospray needle 210. Experimentally this enables delivery of liquid samples with a high percentage of water, and permits enhanced flow rates of liquid to the electrospray needle 210. Water solvent (over 50% water) and high flows of liquid (over 5 uL/min) through typical electrospray needles is accompanied by inefficient droplet desolvation. The jet of heated gas 208 shown at FIG. 9 is designed to assist in desolvation in these cases. The temperature of the heated gas is controlled and is optimized for particular solvents and/or analyte compounds.

The hot gas jet 208 shown at FIG. 9 impinges on the plate 212 that separates the side-to-side FAIMS device 204 from the heated electrospray ionization source 200. This plate 212 serves as the curtain plate in that it is held at a voltage such that ions are driven away from the ESI needle 210 to the aperture 214 in the plate 212 and further driven to the ion inlet 202 of the side-to-side FAIMS 204. The plate 212 is susceptible to heating, which in turn causes the temperature of the side-to-side FAIMS device 204 to drift until equilibrium is reached. It is desirable that the side-to-side FAIMS 204 be maintained at a selected temperature within specified tolerances, independent of the temperature of the ion source, and/or independent of the temperature of the hot gas jet 208 being used to desolvate the liquid spray. To this end, a temperature sensor 900 is provided for sensing a temperature that is based upon a temperature within a FAIMS, and for providing an output signal in dependence upon the sensed temperature. The temperature controller is in communication with the temperature sensor and controllably affects the temperature within the FAIMS in response to the output signal of the temperature sensor.

FIG. 9 also shows that the electrically insulating block 216 of FAIMS 204 optionally includes a heat-exchange passage 218 for providing a flow of a heating/cooling fluid to control the temperature of the other FAIMS components.

Figure 10:
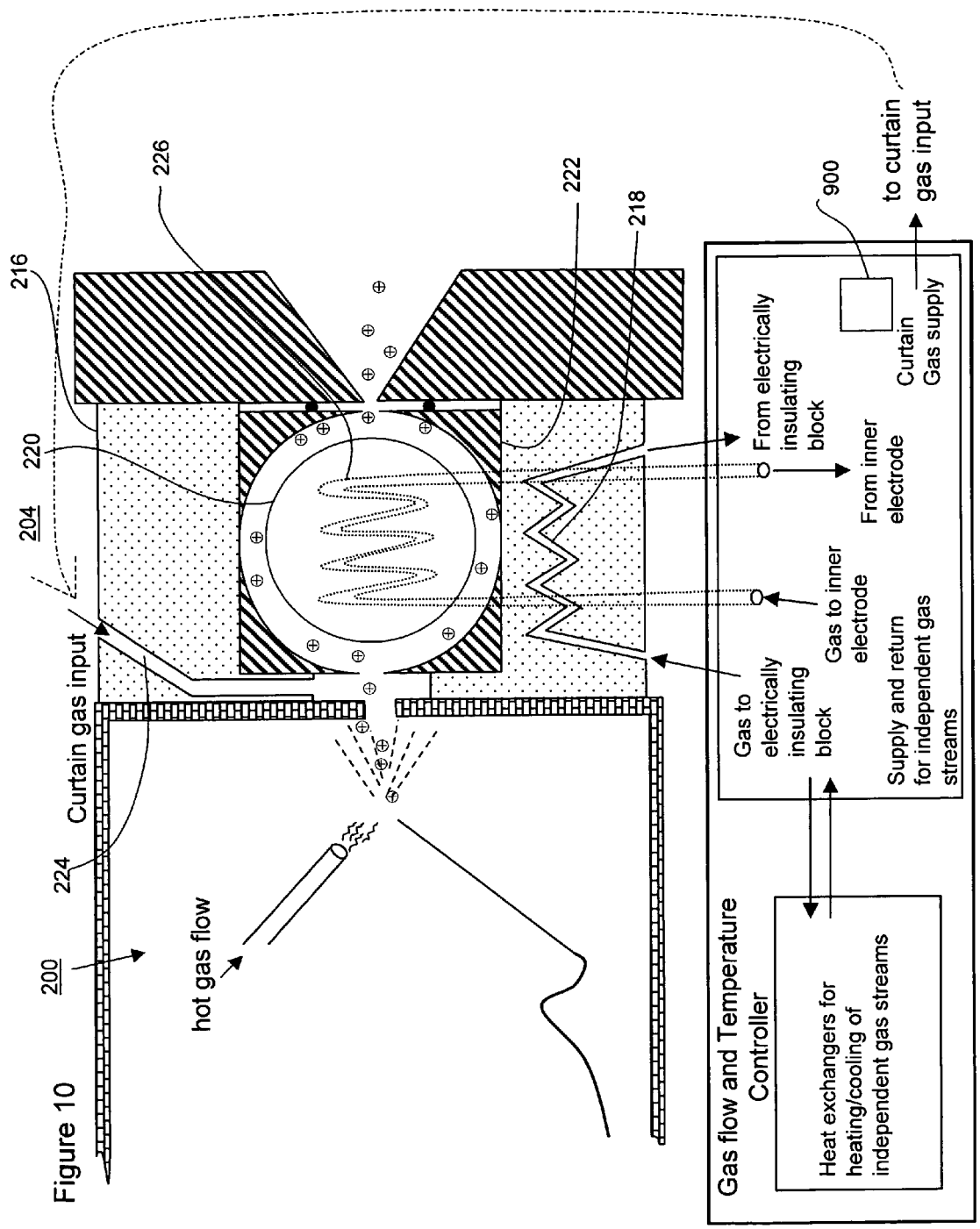
FIG. 10 is a longitudinal cross-sectional view of an apparatus according to an embodiment of the instant invention and including a heated electrospray ionization source that is in fluid communication with an ion inlet of a side-to-side FAIMS including a temperature-controlled inner electrode and temperature-controlled insulating block, in which the temperatures are adjusted using heat-exchange passages.

Referring now to FIG. 10, shown is a longitudinal cross-sectional view of an apparatus according to an embodiment of the instant invention and including a heated electrospray ionization source in fluid communication with an ion inlet of a side-to-side FAIMS with a temperature-controlled inner electrode. Using a temperature controller, it is beneficial to controllably affect the temperatures of the three flows of gas, i) the first flow of gas to the interface between the ion source and the ion inlet of the FAIMS device (the curtain gas), ii) the second flow of gas (or of a liquid) to a heat exchanger region inside the inner electrode 220 and iii) the third flow of gas (or of a liquid) to a heat exchanger region in the outer electrode 222 and/or the electrically insulating block 216 supporting the outer electrode 222.

The temperature of the curtain gas is important because this gas affects the heating/cooling, and therefore the temperature, of the region where the ion source is adjacent to the FAIMS ion inlet. In addition, the curtain gas divides into a portion that enters the side-to-side FAIMS device 204 to carry the ions between the electrodes and a portion that flows into the ion source region 200. In one optional approach of controlling the temperature of the curtain gas, the conduit 224 for the curtain gas passes through the outer electrode 222 and/or through the electrically insulating block 216 prior to entering the curtain region. In this way the gas has reached a temperature approximately equal to the temperature of one of these FAIMS components.

Optionally, the temperature of the gases that return from the side-to-side FAIMS 204 are monitored, for example using a temperature sensor 900, so as to sense a temperature relating to a temperature within the side-to-side FAIMS 204. The temperature sensor produces an output signal which is communicated to the temperature controller. In this case, it is possible to provide feedback control, whereby the ingoing gas temperature is adjusted at the gas supply source by a temperature controller to accommodate changes in the heat flows into and out of the FAIMS system, for example if the temperature of the hot gas jet used in the ionization source is changed. Since the inner electrode 220 is only mounted at its ends in the side-to-side configuration, optionally an independent gas flow heat exchange system 226 is provided for the inner electrode, separate from that of the electrically insulating block 216, the block being in contact with the components of both the heated electrospray ionization source 200 and of the not illustrated mass spectrometer. It is preferable that the inner electrode 220 be maintained at a selected temperature relative to the temperature of the flow of gas that is carrying the ions through the side-to-side FAIMS 204. These are optionally held at equal temperatures. FIG. 10 illustrates a complete system of gas flow and temperature control for providing the gases (and/or liquids) at appropriate temperatures and flow rates to ensure the stability of the temperature of the components of the FAIMS device.

Still referring to FIG. 10, the temperature of the inner electrode 220 is controlled using a flow of heat exchange fluid through the heat exchanger region 226. Similarly, the temperature of the outer electrode 222 is controlled by the temperature of the electrically insulating block 216 whose temperature is controlled using a flow of heat exchange fluid through the heat exchange passage 218 within the electrically insulating block 216. Optionally, the temperature of the inner electrode 220 and the temperature of the outer electrode 222 are different, thereby forming a gradient in the gas in the analyzer region between these two electrodes. The advantages of forming a temperature gradient in the FAIMS analyzer region, and the theory thereof are discussed in relation to FIGS. 13 to 21.

Figure 11:
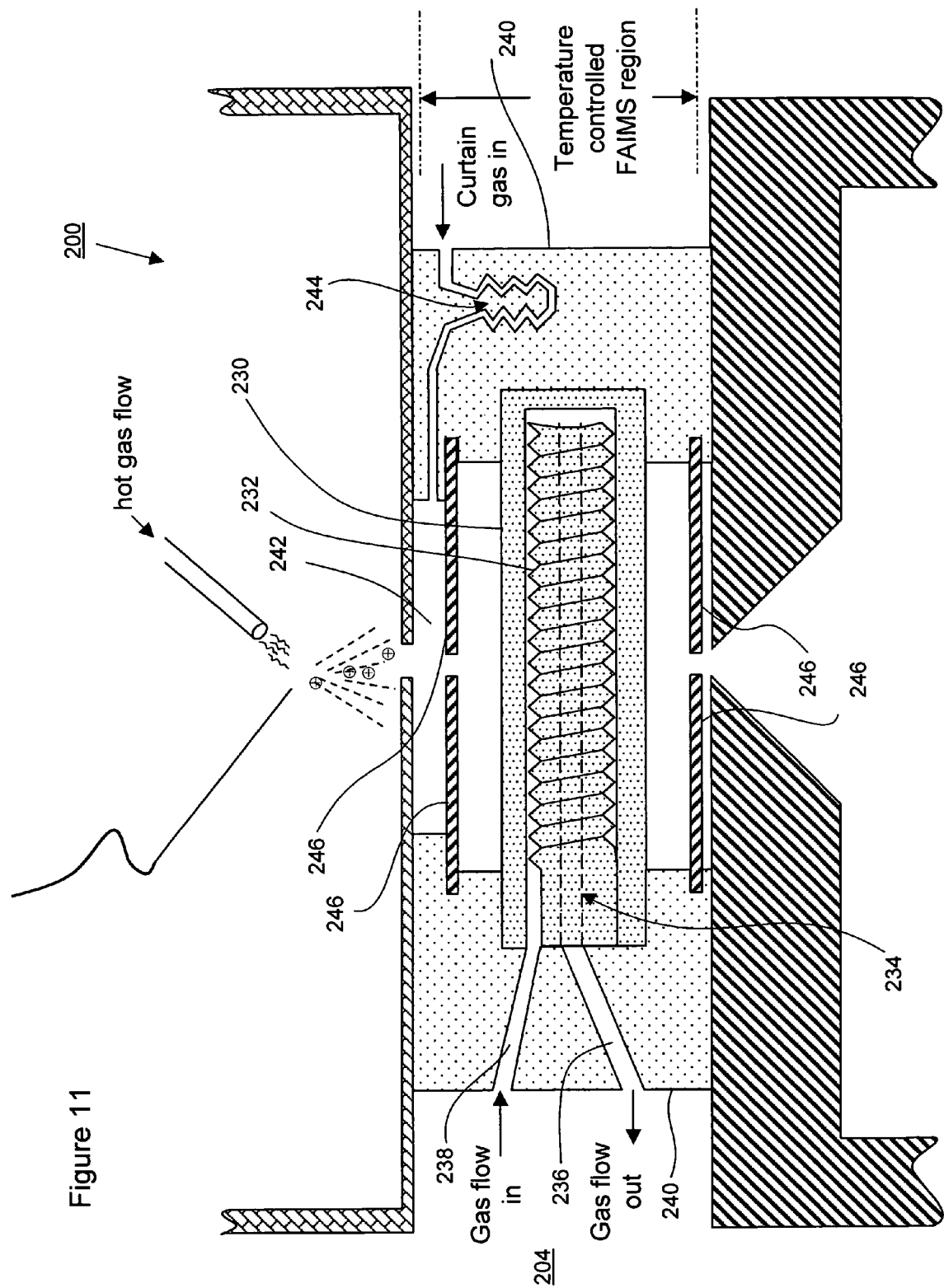
FIG. 11 is a cross-sectional view of the apparatus of FIG. 10, but taken in a plane that is normal to the page of FIG. 10.

Referring now to FIG. 11, shown is a cross sectional view of the heated electrospray ionization source 200 in fluid communication with the side-to-side FAIMS 204 of FIG. 10, but taken in a plane normal to the page of FIG. 10. Accordingly, FIG. 11 illustrates the side-to-side FAIMS device 204 from a second view, in which the cylindrical inner electrode is seen from the side (therefore it looks like a rectangle in FIG. 11). In the instant example, the inner electrode 230 is hollow with a threaded insert 232 for ensuring that a flow of a heat exchange fluid (preferably gas phase but optionally liquid phase) makes maximum contact with the inner electrode 230 prior to returning through a passage 234 drilled through the inner axis of the threaded insert 232. The heat exchange fluid (preferably gas phase but optionally liquid phase) is delivered to the inner electrode through passages 238 in the electrically insulating block 240 and is removed from the inner electrode through passage 236. Optionally, one of these passages 236, 238 includes a heat exchange region prior to or after the heat exchange fluid has passed through the inner electrode 230. The flow of gas to the curtain region 242 is shown to pass through a region 244 that maximizes the contact of the curtain gas with the electrically insulating block 240, thus ensuring the curtain gas is equilibrated to a temperature dependent on the operating temperature of the FAIMS electrodes 230, 246. For simplicity, the flow of heat exchange fluid that heats/cools the electrically insulating block 240 is not shown.

Figure 12:
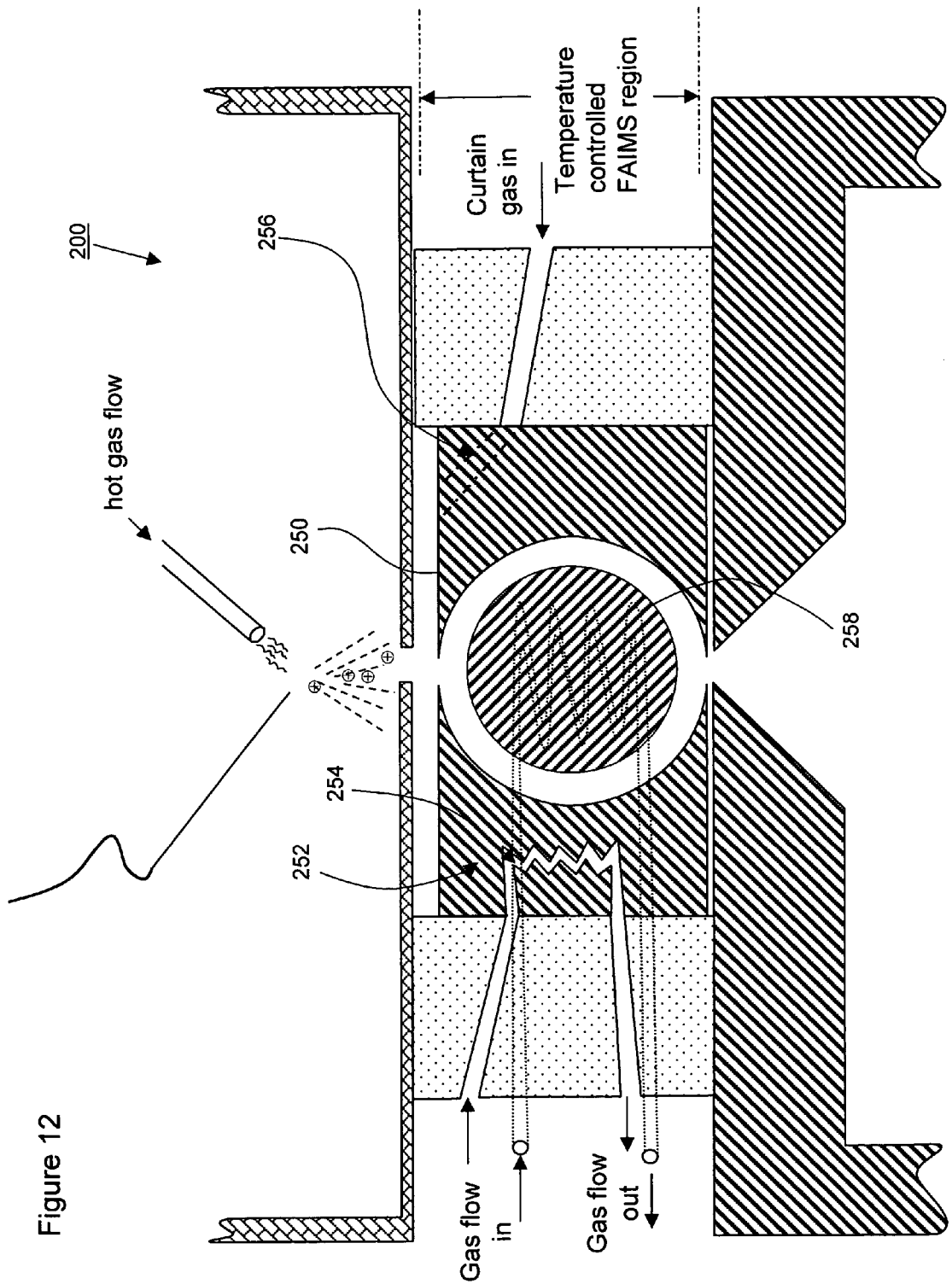
FIG. 12 is a cross-sectional view of an apparatus according to an embodiment of the instant invention and showing the heating/cooling system for the inner and outer electrodes of a side-to-side FAIMS electrode system in which the outer electrode is formed from a rectangular block.

FIG. 12 illustrates the heating/cooling system of a side-to-side FAIMS electrode system in which the outer (electrically conductive) electrode 250 is fabricated as a relatively large rectangular block. This design permits direct heating/cooling of the outer electrode 250 by incorporating a temperature controller (heat exchange region 252) within the body of the outer electrode 250. In practice, for example, this heat exchange process occurs through a series of passageways 254 drilled in the body of the outer electrode 250 in a direction perpendicular to the cross-section of the electrodes shown. FIG. 12 also illustrates that the temperature controller optionally includes a passageway 256 for the curtain gas to pass through a portion of the outer electrode 250, for the purposes of moderating the temperature of the curtain gas to be similar to that of the outer electrode 250. Further optionally, a heating/cooling flow of a heat exchange fluid (preferably gas phase but optionally liquid phase) passes through the inner electrode 258, shown in schematic form in FIG. 12.

Still referring to FIG. 12, the temperature of the inner electrode 258 is controlled using a temperature controller including a flow of a heat exchange fluid through the heat exchanger within the electrode. Similarly, the temperature of the outer electrode is controlled using a temperature controller including a flow of a heat exchange fluid through a passageway 254 (part of heat exchanger region 252) within the outer electrode 250. Optionally, the temperature of the inner electrode 258 and the temperature of the outer electrode 250 are different, thereby forming a temperature gradient in the gas in the analyzer region between these two electrodes. The advantages of forming a temperature gradient in the FAIMS analyzer region, and the theory thereof are discussed below.

The side-to-side FAIMS device illustrated in FIGS. 8 through 12 is provided as a non-limiting example of a FAIMS device for use with the embodiments of the instant invention. Of course, other FAIMS electrode geometries are intended to be encompassed by the instant invention, including as some non-limiting examples: concentric cylinder geometry electrodes with or without a domed inner electrode; flat or curved parallel plate geometry electrodes; and spherical electrodes.

Figure 13:
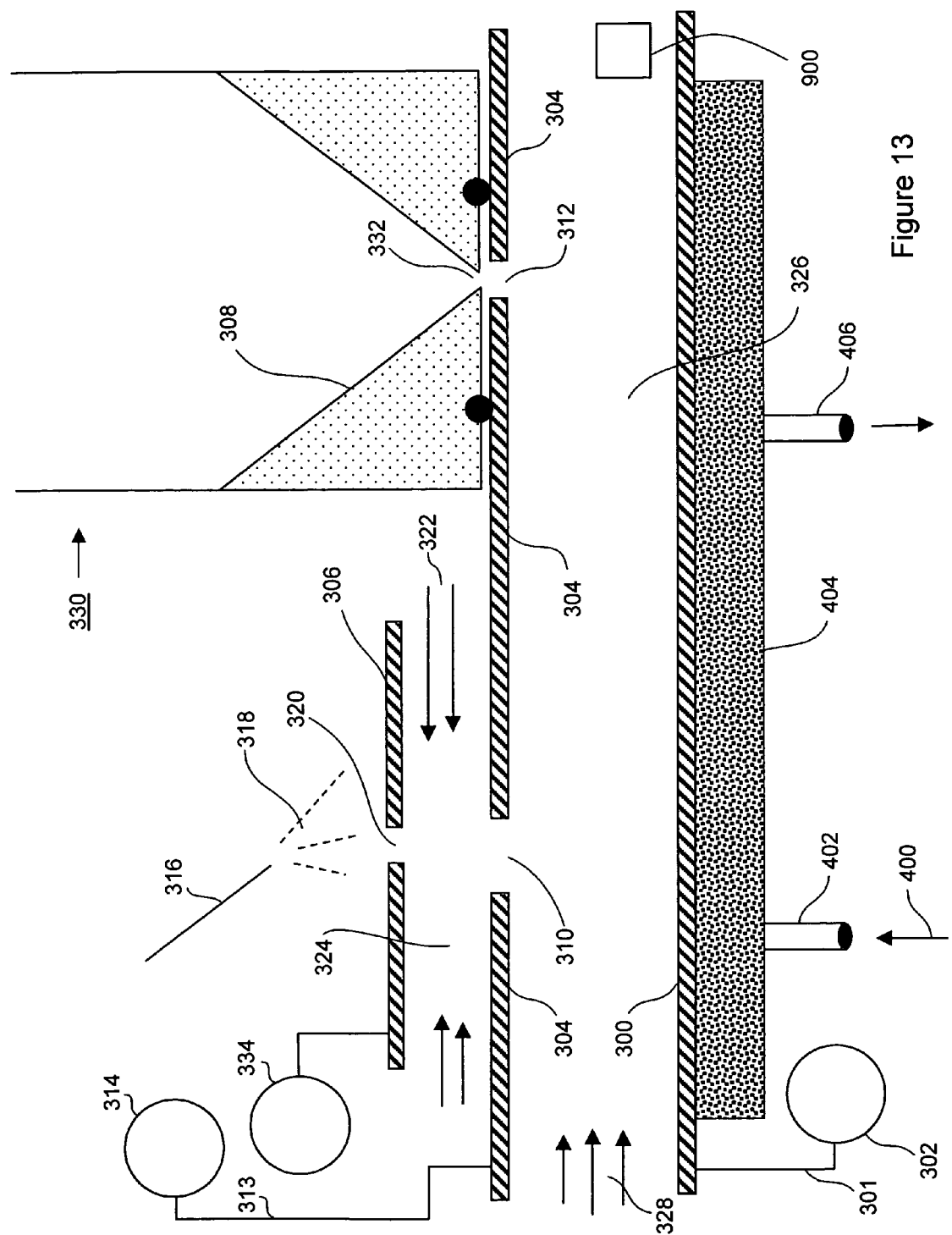
FIG. 13 is a simplified block diagram showing a parallel flat-plate FAIMS including means for establishing a temperature gradient across the analyzer region.

FIG. 13 illustrates one possible design of a parallel flat-plate FAIMS device that uses a temperature gradient across the analyzer region to affect ion focusing. The asymmetric waveform is applied to plate 300 through an electrical coupling 301 to power supply 302. The asymmetric waveform and the compensation voltage (CV) are preferably applied to the same plate 300. Although it is possible to apply the waveform and CV to the other flat plate 304, this is not preferred since the waveform and CV voltages on plate 304 generate unfavorable electric fields between the plate 304 and the curtain plate 306 and between the plate 304 and the sampler cone 308. These fields interfere with the stream of ions that is flowing towards ion inlet 310 and out of the ion outlet 312, respectively.

Referring still to FIG. 13 a selected dc voltage is applied to flat plate 304 via an electrical coupling 313 to a power supply 314. The spacing between plate 304 and plate 300 (the FAIMS electrodes), the applied voltages and the gas pressure are selected to be appropriate for ion separation by the FAIMS mechanism in the analyzer region 326. As mentioned above, the plate 304 has two openings, an ion inlet 310 and an ion outlet 312.

Referring still to FIG. 13 a mixture of ions is formed by an ionization source 316, which in this diagram is illustrated to be an electrospray needle as a non-limiting example of an ionization source suitable for use with the apparatus illustrated in FIG. 13. The ions (of appropriate polarity) in the ion/droplet electrospray plume 318 are driven toward the curtain plate 306 by the electric field between the electrospray needle 316 and the curtain plate 306. Some of the ions pass through the curtain plate orifice 320. A flow of curtain gas 322 is supplied to the curtain region 324 between the curtain plate 306 and the flat plate 304. The voltage supplied to the curtain plate 306 via power supply 334 is used to further direct the ions in the direction of the flat plate 304. Some of the ions pass into the ion inlet 310 and are separated in the analyzer region 326 between the flat plate 304 and the flat plate 300.

The curtain gas 322 supplied to the curtain region 324, splits into two flows, the first exiting through the curtain plate orifice 320 and flowing in a direction counter-current to the ions arriving at the curtain plate orifice 320, and the second flow entering the FAIMS analyzer region 326 through the ion inlet 310. This second flow is combined with an optional carrier gas 328 and this summed gas flow serves to carry the ions along the analyzer region 326 to the ion outlet 312. The ion detection system 330 is preferably a mass spectrometer but optionally is an electrometric or optical detection system, as some non-limiting examples. The detection system 330 shown in FIG. 13 includes a sampler cone 308 that is in gas-tight connection to the flat plate 304. The gas and ions from the analyzer region 326 flow into the sampler cone 308 since the mass spectrometer 330 is operated at reduced pressure and pulls the ions and gas out of the analyzer region through ion outlet 312. Since the mass spectrometer 330 is mounted in gas tight connection to the flat plate 304, the flow rate of gas through the analyzer region 326 is controlled by the flow rate of gas pulled into the vacuum system of the mass spectrometer 330 through the orifice 332. The flow rate into the vacuum system of the mass spectrometer 330 is controlled by the dimensions of the orifice 332 in the sampler cone 308, and by the composition, pressure and temperature of the gas flowing through the analyzer region 326.

Referring still to FIG. 13, a temperature controller including a heat exchanger 404 is also provided for controlling the temperature of the flat plate 300. A heat exchanger fluid 400 is provided to a fluid inlet 402 in the heat exchanger 404. The fluid 400 is transported through heat exchanger 404 and exits via fluid outlet 406. A not-illustrated system pumps the heat exchanger fluid 400, and adds or removes heat from the fluid 400, to allow the temperature of the heat exchanger 404 and of the flat plate 300 to be selected and maintained within selected tolerances. Optionally, a not illustrated temperature sensor is provided for sensing a temperature that is based upon a temperature within the FAIMS, and for providing an output signal in dependence upon the sensed temperature. In this case, the temperature controller is in communication with the temperature sensor and controllably affects the temperature within the FAIMS in response to the output signal of the temperature sensor. For clarity in this figure, an optional heat exchange system for control of the temperature of plate 304 is not shown.

As is discussed below in greater detail, setting the flat plate electrode 304 and the flat plate electrode 300 to different temperatures, so as to establish a temperature gradient in the gas therebetween, results in the establishment of a gradient in the electric field, E/N, between the electrode plates. As a consequence of the gradient of E/N, the ion focusing mechanism of FAIMS becomes operative. This is a significant advantage of the instant invention because in the absence of temperature gradients, the flat plate geometry of FAIMS was not previously expected to exhibit ion focusing behavior. As a result of the temperature gradient being established, and the associated gradient of E/N, ions transmitted at the applied voltage of asymmetric waveform and compensation voltage are focused as they travel between the flat plates. This results in increased ion transmission efficiency since ion loss through mechanisms of diffusion and space charge ion-ion repulsion (as some non-limiting examples of mechanisms of ion loss) is minimized.

Advantageously, the ability to controllably affect the temperature of each of the FAIMS electrodes supports a method for separating ions with controllably variable ion focusing strength. This method is discussed in conjunction with the following figures, in which a series of non-limiting examples is depicted for the purpose of facilitating a better understanding the instant invention.

Figure 14:
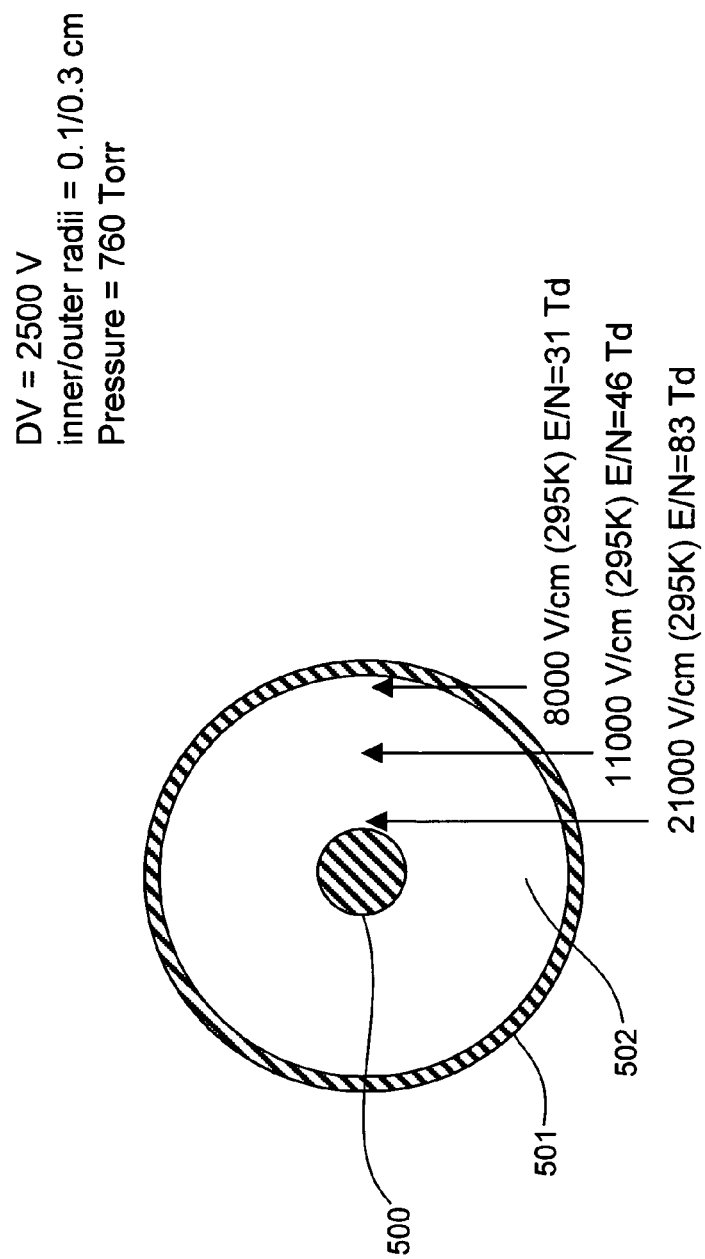
FIG. 14 is a simplified end view of a cylindrical geometry FAIMS having an inner electrode and an outer electrode of radii 0.1 cm and 0.3 cm, respectively, and showing calculated electric field (E/N) values at about 5%, 50% and 95% of the distance from the surface of the inner electrode to the surface of the outer electrode, absent a temperature gradient.

FIG. 14 illustrates (not to scale) an end view of a cylindrical geometry FAIMS with inner electrode 500 and outer electrode 501 in concentric arrangement and a FAIMS analyzer region 502 defined by the annular space between the inner electrode 500 and the outer electrode 501. The electric field E/N measured in Townsend (Td) is defined as $(E/N) \times 10^{17}$ where E is the electric field in volts/cm and N is the number density of the gas (molecules/cc). The electric field E/N was calculated at three different radial locations in the analyzer region 502, at about 5%, 50% and 95% of the distance from the surface of the inner electrode 500 to the surface of the outer electrode 501. The spacing and voltages, and physical dimensions, and conditions of gas pressure and temperature are as follows: inner electrode 500 radius=1 mm; outer electrode 501 radius=3 mm; space 502 between electrodes=2 mm; voltage applied to the inner electrode=±2500 volts; gas pressure=760 torr; and, uniform gas temperature=295 K. In the region near the inner electrode 500 the electric field was calculated to be about 83 Td whereas the electric field at about 95% of the distance to the outer electrode was 31 Td. This decrease in field strength in the space between the electrodes is well known for the cylindrical geometry (and spherical geometry, and for several other arrangements of electrodes having curved electrode surfaces). The change in electric field E/N is responsible for the ion focusing properties that are known to exist in a cylindrical geometry of FAIMS. Of course, any operating parameter which gives rise to a non-constant electric field E/N supports ion focusing in the FAIMS analyzer region. The ion focusing property is known to reduce loss of ions to the walls of FAIMS, and thereby improves ion transmission efficiency. Many geometrical arrangements of electrodes produce an electric field E/N that varies in strength over a distance, one of the conditions that is required for ion focusing. The conditions of asymmetric waveform and the electric field strengths that are needed for operation of the FAIMS ion separation mechanism are well known. When these conditions of asymmetric waveform and field strengths are applied to an electrode geometry wherein the electric field E/N changes in strength in space it is well known that the ion focusing mechanism of FAIMS becomes operative. Several practical embodiments of ion focusing and ion trapping FAIMS have been reported in the literature, for example Guevremont and Purves, Rev. Sci. Instrum. 1999, 70, 1370–1383 and Guevremont et al., J. Am. Soc. Mass Spectrometry 2001, 12, 1320–1330 and in U.S. Pat. No. 6,621,077 (Sep. 16, 2003), all of which are incorporated herein by reference.

Figure 15:
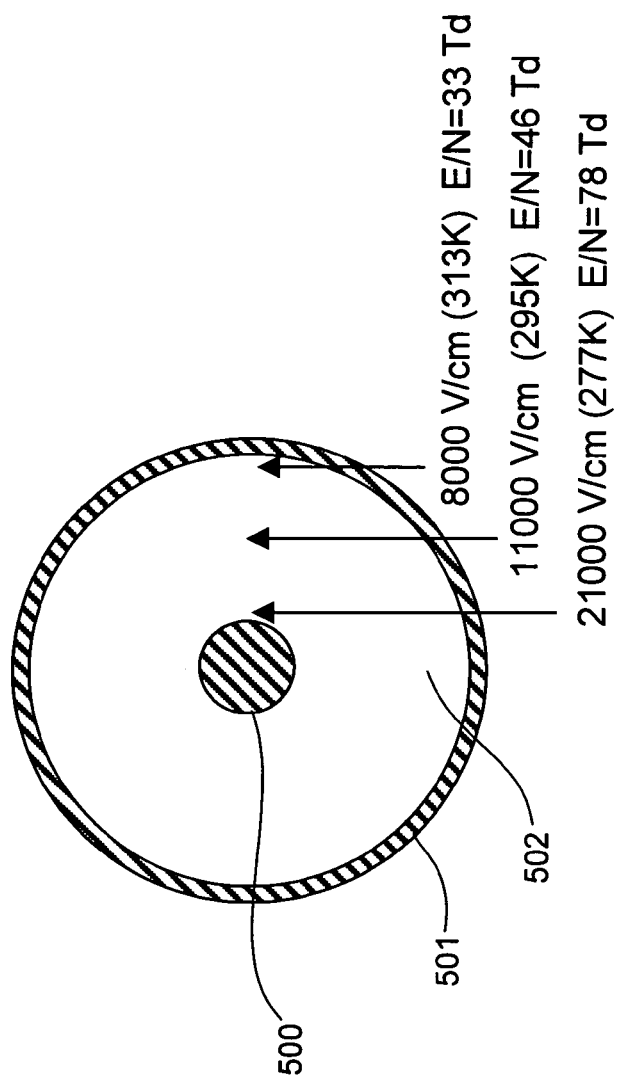
FIG. 15 is a simplified end view of a cylindrical geometry FAIMS having an inner electrode and an outer electrode of radii 0.1 cm and 0.3 cm, respectively, and showing calculated electric field (E/N) values at about 5%, 50% and 95% of the distance from the surface of the inner electrode to the surface of the outer electrode, assuming a +20 K/mm temperature gradient beginning at the inner electrode and with 2500 volts applied between the electrodes.

FIG. 15 closely resembles FIG. 14, but the calculations of the field E/N in FIG. 15 are based on a gas temperature that varies approximately linearly between the inner and outer electrode. This is a first simplifying approximation to a condition wherein the inner electrode 500 and the outer electrode 501 are about 40 degrees Celsius (40 degrees Celsius equals 40 Kelvin (K)) different from each other, and that the gas is equilibrated without turbulence or convective flows so that heat from the hot electrode flows uniformly through the gas and is absorbed by the cooler electrode. Other operating parameters are identical to those of FIG. 14. The spacing and voltages, and physical dimensions, and conditions of gas pressure and temperature are as follows: inner electrode 500 radius=1 mm; outer electrode 501 radius=3 mm; space 502 between electrodes=2 mm; voltage applied=±2500 volts; gas pressure=760 torr. A temperature gradient of +20K/mm starting at 275K at the inner electrode 500 exists. In FIG. 15 the inner electrode 500 is about 40K cooler than the outer electrode 501.

Still referring to FIG. 15, since the temperature of the gas at various radial locations in the analyzer region 502 differ, so does the number density N of the gas. When the field E/N in Td is calculated at the same locations as shown in FIG. 14, with all conditions taken to be the same as in FIG. 14 with the exception of the gas temperature, the electric field values are not identical. The temperature of the gas has altered N, and therefore E/N is not identical in FIG. 14 and FIG. 15. In FIG. 15, wherein the inner electrode 500 is about 40K cooler than the outer electrode 501, the electric field near the inner electrode is lower than that in FIG. 14. Similarly the field E/N near the outer electrode 501 is higher in FIG. 15 than in FIG. 14. This temperature gradient, with inner electrode 500 cooler than outer electrode 501 has the effect of reducing the gradient of E/N between the inner electrode 500 and the outer electrode 501. This reduces the magnitude of the effect of ion focusing when FAIMS is in operation. Reduction of the strength of ion focusing is predicted to result in a wider distribution of the ion cloud in the region 502, resulting in more rapid loss of ions through collisions with the electrodes (lower ion transmission), and is also predicted to narrow the peak widths in the scan of the compensation voltage (CV spectrum).

Figure 16:
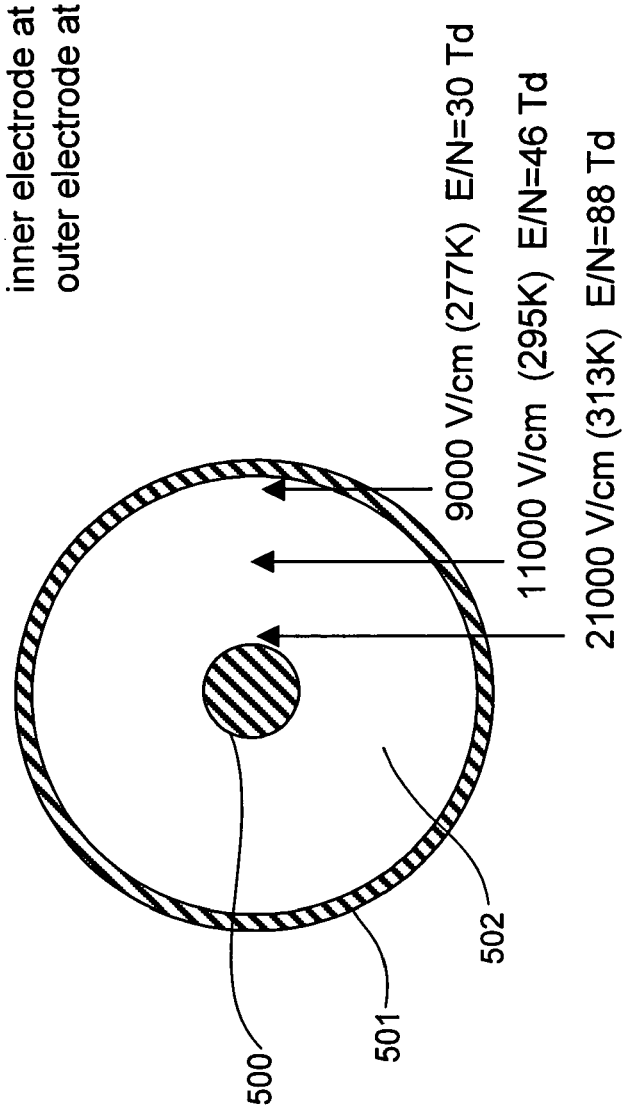
FIG. 16 is a simplified end view of a cylindrical geometry FAIMS having an inner electrode and an outer electrode of radii 0.1 cm and 0.3 cm, respectively, and showing calculated electric field (E/N) values at about 5%, 50% and 95% of the distance from the surface of the inner electrode to the surface of the outer electrode, assuming a −20 K/mm temperature gradient beginning at the inner electrode and with 2500 volts applied between the electrodes.

Referring now to FIG. 16, shown is a repeat of the calculations of FIG. 15, except with the direction of the temperature gradient between the inner electrode 500 and the outer electrode 501 reversed. Other operating parameters are identical to those of FIGS. 14 and 15. The spacing and voltages, and physical dimensions, and conditions of gas pressure and temperature are as follows: inner electrode 500 radius=1 mm; outer electrode 501 radius=3 mm; space 502 between electrodes=2 mm; voltage applied=+2500 volts; gas pressure=760 torr. A temperature gradient of −20K/mm starting at 275K at the inner electrode 500 exists. In FIG. 16 the inner electrode 500 is about 40K hotter than the outer electrode 501. As before, an idealized (as a simplified first approximation) condition of an approximately uniform temperature gradient in the gas across the space of the analyzer region 502 is assumed. When the number density of the gas is calculated for the three locations shown in FIG. 16 (corresponding to the same radial locations discussed in FIGS. 14 and 15), the number density is lowest when the gas is at the highest temperature near the inner electrode 500. This gives an electric field E/N near the inner electrode 500 that is higher than was shown in FIG. 14. Similarly, the electric field E/N near the outer electrode in FIG. 16 is lower than that shown in FIG. 14.

Still referring to FIG. 16, by comparison to FIG. 14, the change of the strength of the electric field E/N between the inner electrode 500 and the outer electrode 501 is more pronounced when the gas temperature varies from hot near the inner electrode 500 to cooler near the outer electrode 501 (FIG. 16), than when the temperature is uniform across the analyzer region 502 (FIG. 14). An increase in the gradient of the strength of electric field E/N is expected to increase the effect of ion focusing in the analyzer region 502. This results in fewer ions being lost to the walls of the electrodes, and better ion transmission through FAIMS. The temperature gradient shown in FIG. 16 augments, or increases, the gradient of E/N inherently formed within the cylindrical geometry FAIMS.

As shown in FIGS. 14, 15 and 16, the selection of the temperatures of the inner electrode 500 and outer electrode 501 is used to affect the performance of FAIMS. Of course, in a practical chemical analysis the requirements of transmission efficiency and CV peak widths depend upon the application and the particular type of ion analysis being performed. By improper selection of the temperatures of the electrodes, it is possible to significantly adversely affect ion transmission. It was discussed earlier that preferably the CV of transmission of a selected ion be maintained throughout the path of transmission of the selected ion. In one approach, the temperature of one electrode is adjusted to be higher than the temperature of the carrier gas, whereas the temperature of the other electrode is adjusted to be lower than the temperature of the carrier gas. By adjustment of the temperatures, equal heat is provided to the gas by the higher temperature electrode as is removed by the lower temperature electrode. Since no net heat is added or removed from the gas, the average gas temperature is maintained (although regions near the electrodes deviate from this average temperature), and the CV of the transmission of the selected ion does not shift. In practice, the temperatures of the electrodes are adjusted, and ion transmission monitored, to obtain a desired degree of ion transmission and the desired width of the peaks in the CV spectrum that meet the needs of the particular chemical analysis application.

Figure 17:
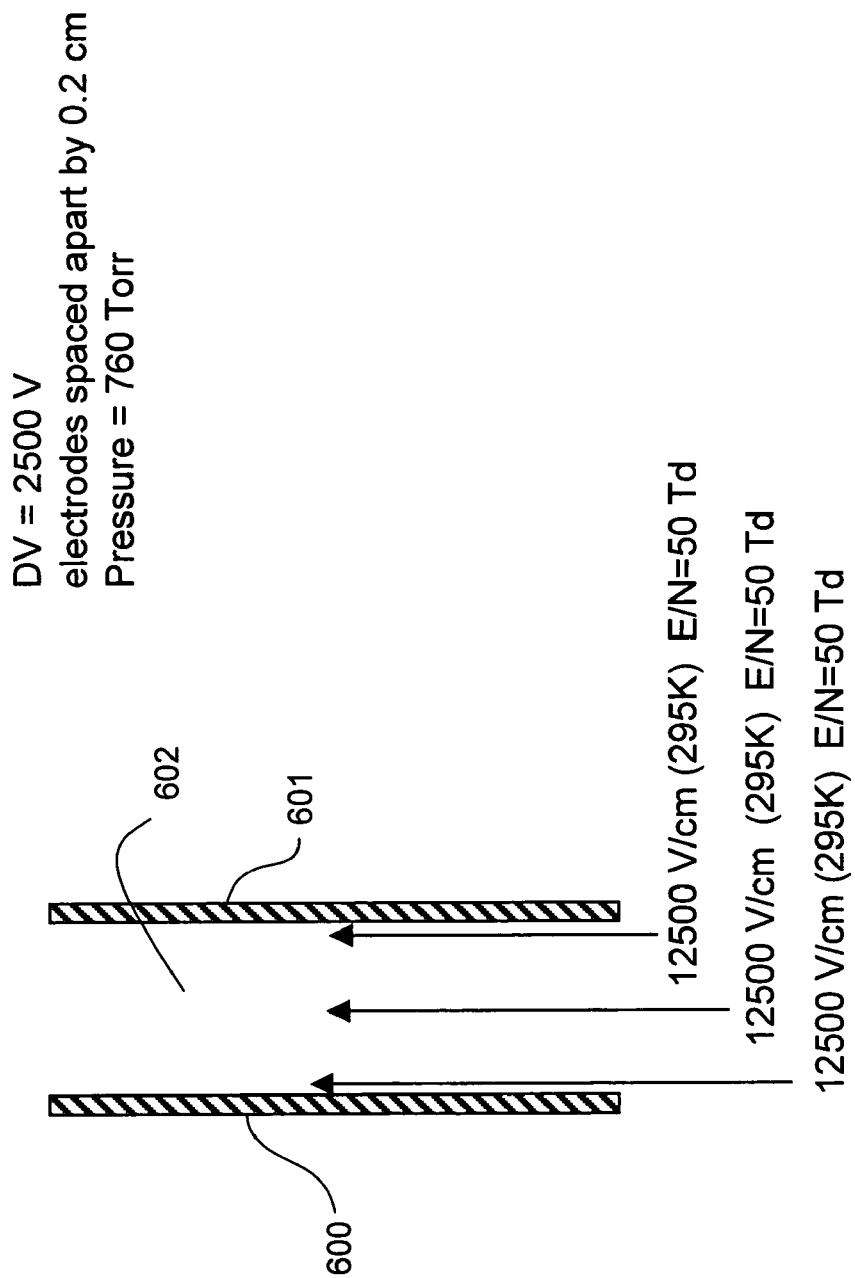
FIG. 17 is a simplified end view of a parallel flat-plate FAIMS having a first electrode and a second electrode spaced apart by 0.2 cm, and showing calculated electric field (E/N) values at about 5%, 50% and 95% of the distance from the surface of the first electrode to the surface of the second electrode, absent a temperature gradient and with 2500 volts applied between the electrodes.
Figure 18:
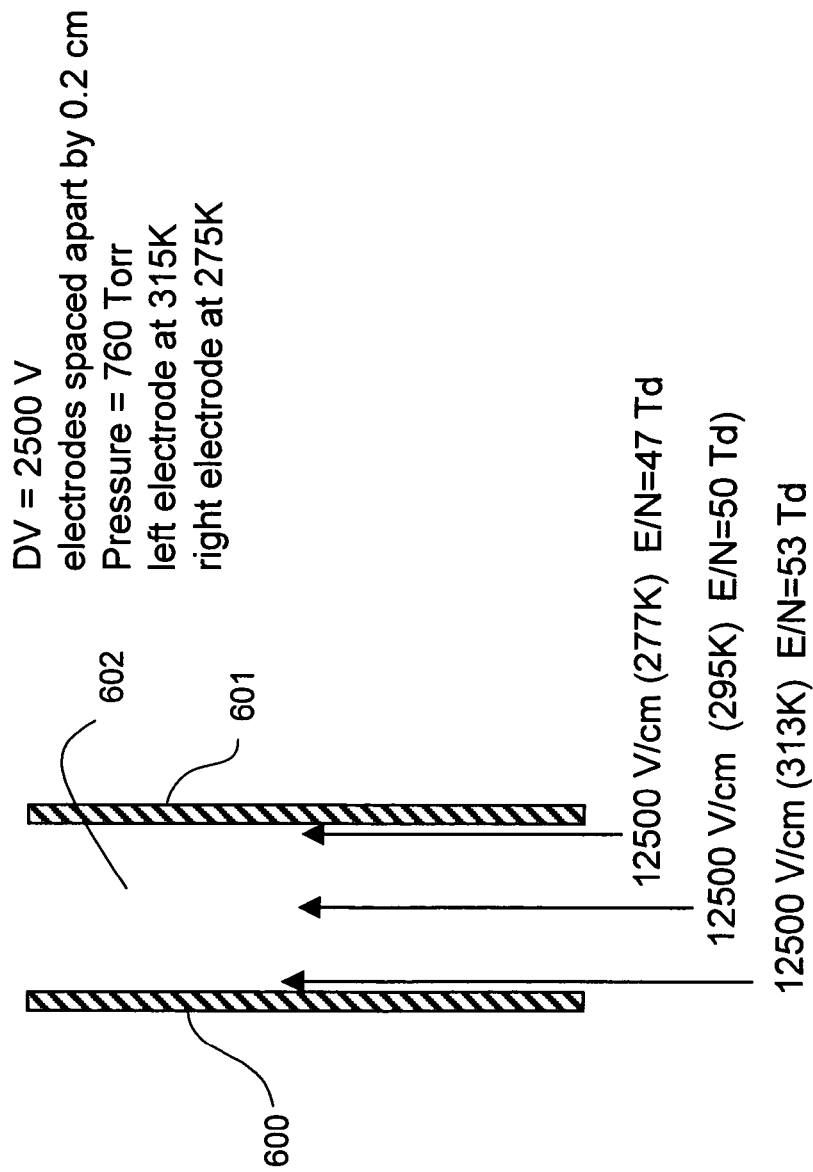
FIG. 18 is a simplified end view of a parallel flat-plate FAIMS having a first electrode and a second electrode spaced apart by 0.2 cm, and showing calculated electric field (E/N) values at about 5%, 50% and 95% of the distance from the surface of the first electrode to the surface of the second electrode, assuming a −20 K/mm temperature gradient from left to right in the Figure and with 2500 volts applied between the electrodes.

FIGS. 17 and 18 are comparable to FIGS. 14 to 16, but with the cylindrical FAIMS electrodes of FIGS. 14 to 16 replaced by parallel flat-plate electrodes. Since the electric field between two parallel flat-plates (away from edges) is uniform, the FAIMS ion focusing mechanism typical of cylindrical electrode geometry is not normally expected to function between parallel flat-plates (away from edges). Referring now to FIG. 17, the electric field E/N is calculated within the analyzer region 602 at locations about 5%, 50% and 95% of the distance between a left flat plate 600 and a right flat plate 601. The conditions of electrode spacing, voltages, gas pressure and temperature are as follows: left electrode=flat plate; right electrode=flat plate; space between electrodes=2 mm; voltage applied=2500 volts; pressure=760 torr; and, uniform gas temperature=295K.

Still referring to FIG. 17, the field strength E/N is about 50 Td, at all points between the left plate 600 and right plate 601.

FIG. 18 is similar to FIG. 17 except that the temperature of the left electrode 600 is about 40K hotter than the right electrode 601 and the gas temperature varies linearly between these temperatures in the analyzer region 602 between the left electrode 600 and the right electrode 601. The electric field E/N was calculated at the same locations relative to the electrodes as in FIG. 17, but since the temperature of the gas is not uniform across the analyzer 602, the values of E/N near the left electrode 600 is higher than near the right electrode 601. This mimics the gradient of E/N typically found in the annular region between concentric cylinders, and the gradient of E/N is suitable for focusing of ions. This is the first report of a method and apparatus for focusing of ions in the space between parallel flat-plate electrodes. The FAIMS mechanism of ion focusing in this new case of parallel flat-plates held at differing temperatures (with a gradient of gas temperature between the plates) is identical to that previously described for cylindrical geometry wherein the gradient of E/N forms simply because of the electrode geometry.

FIG. 19 illustrates a comparison between the gradients of electric field E/N formed with parallel flat-plates held at differing temperatures, and the gradients of electric field E/N formed with concentric cylinders held at uniform temperature. As shown at part a) of FIG. 19, the left plate 600 is held at 40K hotter than the right plate 601, and a uniform temperature gradient in the gas is formed across the analyzer region 602 between the parallel flat-plates. The field strength E/N near the left plate 600 is about 53 Td, near the middle is about 50 Td and near the right plate 601 is about 47 Td. This corresponds to a gradient of E/N of about 3 Td per mm. If, as shown at part b) of FIG. 19, cylindrical geometry electrodes are operated at constant temperature, with the same voltage and mechanical distances between the electrodes, a change of E/N of about 4 Td per mm is formed when the inner electrode 605 is about 10 mm radius and the outer electrode 606 is about 12 mm radius. The change of E/N per radial distance decreases as the radii of the electrodes is increased while maintaining the same spacing (i.e., as the curvature of the surfaces of the concentric cylinders begins to decrease and the surfaces begin to approximate the equivalently spaced parallel flat plates). The strength of the ion focusing effect in FAIMS is known to decrease in strength as the gradient of E/N decreases.

Preferably, independent control of the temperature of the FAIMS electrodes is used to produce a temperature gradient in the gas in the analyzer region between the electrodes. Several examples of means for the independent control of the temperatures of these electrodes have been shown in FIGS. 5 (domed electrodes), FIGS. 10, 11 and 12 (side-to-side FAIMS electrodes) and FIG. 13 (flat parallel plate FAIMS). Optionally, the temperature controller is for controllably affecting the temperature of the flow of a gas that is introduced into the analyzer region of FAIMS. For instance, the temperature controller provides a plurality of separate streams of gas, each stream of the plurality being adjusted to a different temperature prior to being introduced into the analyzer region of FAIMS. The streams are introduced into the analyzer region, absent turbulence, such that a first gas flow at a first temperature is adjacent a first electrode and a second gas flow at a second temperature is adjacent the second electrode. This is one non-limiting example of a method of establishing a temperature gradient within the FAIMS analyzer region without varying the temperatures of the first and second FAIMS electrodes.

In many cases it is beneficial to maximize the gradient of E/N to maximize ion focusing and thereby minimize ion loss to the electrode surfaces. The combination of cylindrical (or spherical) geometry with small radii, and the formation of temperature gradients (with maximum temperature differences) provides an approach for increasing the strength of the FAIMS ion focusing capability.

Figure 20:
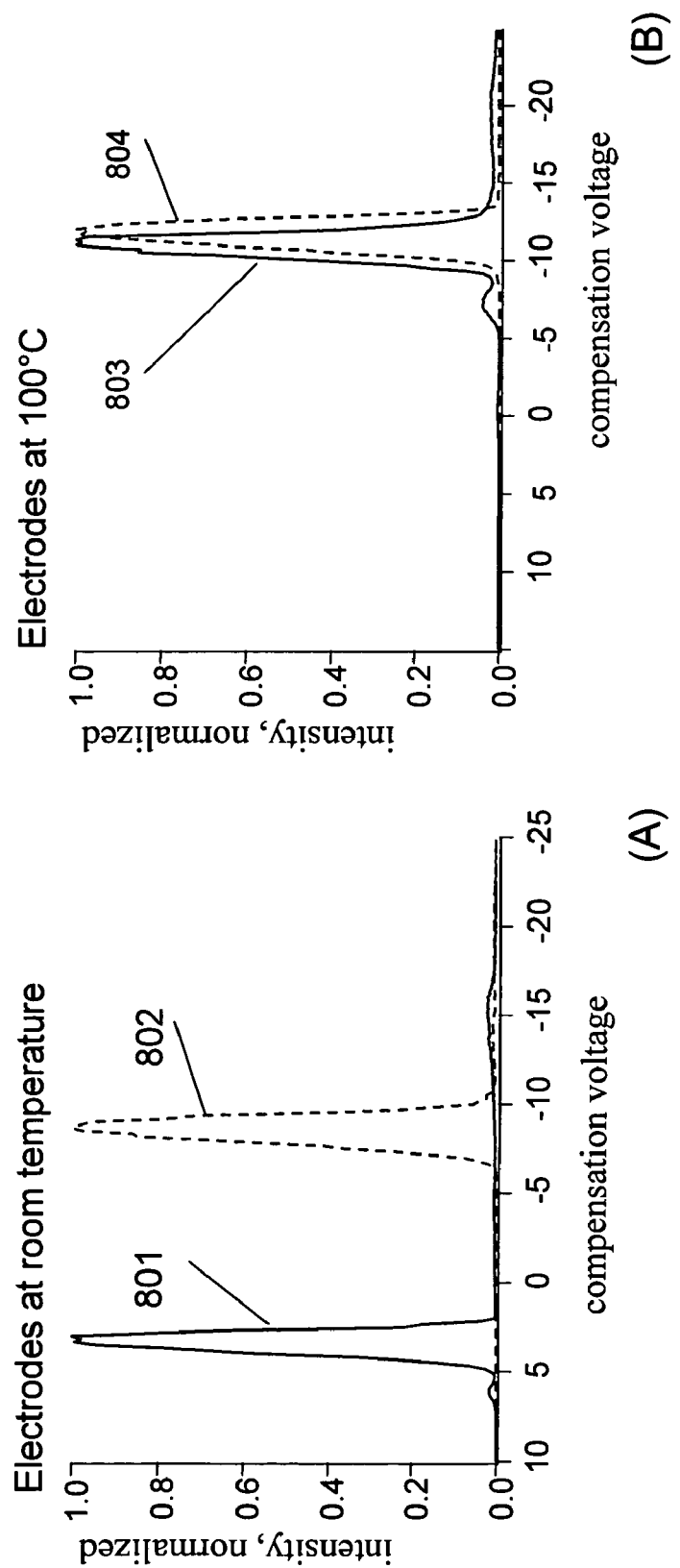
FIG. 20 presents experimental data collected with an embodiment of the present invention showing the separation capability of a FAIMS analyzer in dependence of the temperature within the analyzer region with a) electrodes at room temperature and b) electrodes at 100° C.

FIG. 20 illustrates experimental data that was collected using an apparatus according to an embodiment of the instant invention. Ions of acetaminophen and reserpine were generated by electrospray ionization and introduced into a cylindrical geometry FAIMS with the side-to-side configuration similar to that shown in FIGS. 8a and 8b. The asymmetric waveform and compensation voltage were applied to the inner electrode. Independent flows of gas were passed through flow controllers including heating cartridges and subsequently were directed into the inner cylindrical electrode and independently into the outer electrode heat exchange regions in a manner similar to that shown in FIG. 12. The temperature of the gas flowing into the FAIMS electrodes and out of the electrodes was monitored. The outer electrode temperature was measured and recorded, and the temperature of the inner electrode was inferred from the temperature of the gas exiting from the inner electrode. The compensation voltage was scanned while monitoring the acetaminophen ion and monitoring the reserpine ion with a Sciex API150 single quadrupole mass spectrometer.

Referring now to part A of FIG. 20, shown are experimental results obtained with FAIMS operating at room temperature (about 295K). A first trace of the compensation voltage scan while detecting acetaminophen ion using the mass spectrometer is shown as trace 801 and a second trace of the compensation voltage scan while detecting reserpine ion using the mass spectrometer is shown as trace 802. In the first trace 801, the acetaminophen ion is transmitted through FAIMS at a compensation voltage of approximately +4 volts under ambient conditions of temperature and pressure, a pre-determined gas composition, and a predetermined DV. In the second trace, the reserpine ion is transmitted through FAIMS at a compensation voltage of approximately −8 volts under the same ambient conditions of temperature and pressure, a pre-determined gas composition, and a predetermined DV.

Referring now to part B of FIG. 20, shown are experimental results for a second experiment at the same gas composition and DV as used in part A, and conducted with application of heat to both the inner and the outer FAIMS electrodes. Two independent flows of gas were each passed through flow controllers and electrically powered heating cartridges and subsequently were directed into the inner cylindrical electrode heat exchange region and independently into the outer electrode heat exchange regions in a manner similar to that shown in FIG. 12. The temperature of the gas flowing into the FAIMS electrodes and out of the electrodes was monitored. The outer electrode temperature was measured and recorded, and the temperature of the inner electrode was inferred from the temperature of the gas exiting from the inner electrode. The monitored temperatures were both 100° C. (373K). The compensation voltage was scanned to determine experimentally the compensation voltage at which acetaminophen ion and the reserpine ion were transmitted through FAIMS and the resulting ion signals are shown as traces 803 and 804, respectively.

The data in FIG. 20 illustrates an example in which the selection of the temperature of the FAIMS electrode offers the opportunity to adjust the separation of compounds of interest. In other words, temperature has unpredictable effects on the change of mobility in high electric fields and therefore changes in temperature are used beneficially for controlling the separation of ions. The separation of acetaminophen and reserpine cannot be done at 373K whereas setting the temperature of the FAIMS electrodes to room temperature (about 295K) permitted the separation of these two compounds.

Still referring to FIG. 20, there are several benefits of controlling the temperature of FAIMS. Some of the benefits are widely known and are important for the practical application of FAIMS. In a first example, it is beneficial that the FAIMS remain at constant temperature so that the CV of transmission of the ion of interest remains consistent and reproducible. In a second example, it is beneficial that the temperature remain constant when the temperature of other components of the system are changed, namely that FAIMS is operating at temperatures (and pressures) that are not influenced by adjacent devices. Finally in a third example, it is known in conventional drift tube ion mobility spectrometry that elevated temperature minimizes the formation of complexes between neutral compounds in the gas and the ion of interest, thereby avoiding the widening of peaks that would otherwise occur at lower temperatures. Some of these benefits may be applicable to FAIMS while others are not. However in addition to the benefits noted above, the effect of temperature has new unforeseen and unique consequences in FAIMS. As shown in FIG. 20, the separation of acetaminophen and reserpine is best done at lower temperature. In FAIMS the temperature provides a second-order effect that further modifies the compound-dependent changes in mobility in strong electric fields of the ions, in some cases permitting separations at a second temperature that did not occur at a first temperature. Referring again to FIG. 20, it should also be noted that in this case, contrary to expected effects of temperature in conventional drift tube ion mobility spectrometry, the performance of FAIMS at lower temperatures exceeds that at higher temperatures. Hence, results from conventional drift tube ion mobility spectrometry cannot be reasonably used to predict the effect temperature will have on the capability of FAIMS to achieve a desired separation.

Figure 21:
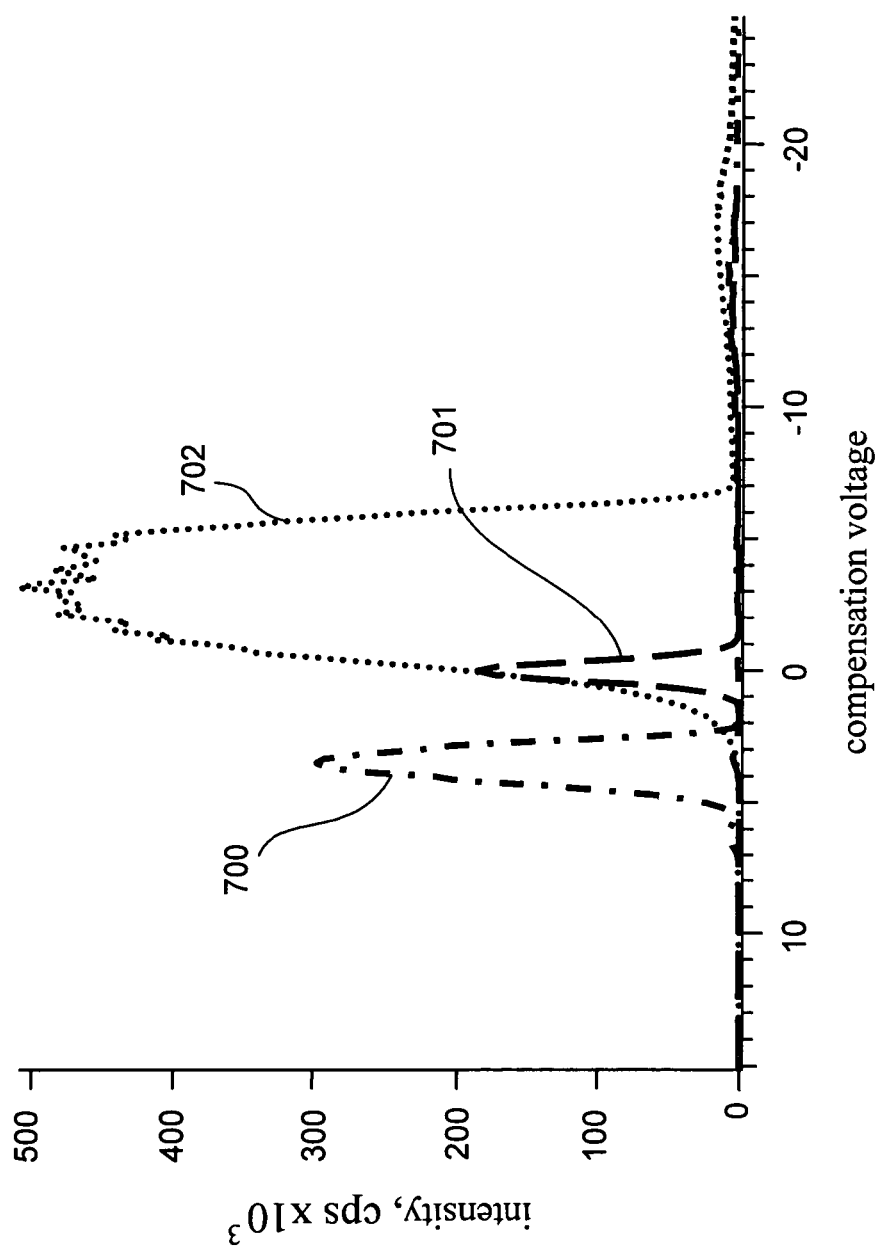
FIG. 21 presents experimental data collected with an embodiment of the present invention showing the dependence of ion transmission on temperature gradients imposed across the analyzer region.

FIG. 21 illustrates experimental data that was collected using an apparatus according to an embodiment of the instant invention. Ions of acetaminophen were generated by electrospray ionization and introduced into a cylindrical geometry FAIMS with the side-to-side configuration similar to that shown in FIGS. 8a and 8b. The asymmetric waveform and compensation voltage were applied to the inner electrode. Independent flows of gas were passed through flow controllers including heating cartridges and subsequently were directed into the inner cylindrical electrode and independently into the outer electrode heat exchange regions in a manner similar to that shown in FIG. 12. The temperature of the gas flowing into the FAIMS electrodes and out of the electrodes was monitored. The outer electrode temperature was measured and recorded, and the temperature of the inner electrode was inferred from the temperature of the gas exiting from the inner electrode. The compensation voltage was scanned while monitoring the acetaminophen ion with a Sciex API150 single quadrupole mass spectrometer.

Still referring to FIG. 21, a first experiment was conducted without any heating to FAIMS or to the ionization source, and a first trace of the compensation voltage scan while detecting acetaminophen ion by the mass spectrometer is shown as trace 700 on FIG. 21. In the first experiment, the acetaminophen ion is transmitted through FAIMS at a compensation voltage of approximately +4 volts under ambient conditions of temperature, pressure, a pre-determined gas composition, and a predetermined DV.

Still referring to FIG. 21, a second experiment at the same gas composition and DV was conducted by application of heat to the outer FAIMS electrode while allowing the inner electrode to remain near room temperature. The compensation voltage was scanned to determine experimentally the compensation voltage at which acetaminophen was transmitted through FAIMS and the resulting ion signal shown as trace 701 in FIG. 21. Trace 701 was collected while the outer electrode was approximately 58° C. (331K) and the inner electrode near room temperature (295K). The peak in trace 701 is narrower than the trace 700 collected without a temperature difference between the inner and outer electrodes, and the signal intensity of trace 701 is lower than that of trace 700.

Referring again to FIG. 21, a third experiment at the same gas composition and DV was conducted by application of heat to the inner electrode while allowing the outer electrode to remain near room temperature. The compensation voltage was scanned to detect the compensation voltage at which acetaminophen was transmitted through FAIMS and the resulting ion signal is shown as trace 702 in FIG. 21. Trace 702 was collected while the inner electrode was approximately 100° C. (373K) and the outer electrode near room temperature (295K). The peak in trace 702 is wider than the trace 700 collected without a temperature difference between the inner and outer electrodes, and the signal intensity of trace 702 is higher than that of trace 700.

The data in FIG. 21 illustrate examples in which the selection of the temperature of one electrode to be different than the temperature of the other electrode offers the opportunity to adjust the peak width in the compensation voltage scan and the sensitivity of the measurement of the ion of interest. In other words, temperature gradients in the gas between the electrodes beneficially affect the ion focusing mechanism of FAIMS and beneficially affect the peak widths and sensitivity as shown in FIG. 21. The user of FAIMS selects the peak width and sensitivity that is appropriate for a chemical analysis application, and adjusts the temperature and/or temperature gradient of the FAIMS to achieve the specified performance for the application.

It is an unexpected benefit of the utilization of a temperature gradient between the electrodes that the ion focusing mechanism of FAIMS is operative in electrode geometries which were previously unable to provide ion focusing. Although very few electrode geometries have been discussed in detail in this document, those skilled in the art will be able to apply the concepts of utilization of temperature gradients to modify E/N gradients in those geometries that inherently exhibit E/N gradients (including cylindrical, and spherical geometries as non-limiting examples). Similarly it will be recognized that the skilled worker will readily understand the utilization of temperature gradients to generate E/N gradients in those geometrical arrangements of electrodes that previously lacked such an E/N gradient, thereby permitting those geometries to be used in FAIMS with the beneficial effects of ion focusing. The skilled worker will also be able to strategically apply the concepts of temperature gradients in electrode geometries which include both one or more regions lacking inherent gradients of E/N as well as, elsewhere in the same geometries, one or more regions that have inherent gradients of E/N because of non parallel or curved electrode surfaces in such a way as to beneficially affect ion transmission efficiency and ion separation capability of the FAIMS system.

The apparatus of the instant invention supports a novel approach for improving the separation capability of a FAIMS analyzer. As discussed above in reference to FIG. 20, the effect of the temperature within the FAIMS analyzer region on the capability of FAIMS to achieve a desired separation cannot be predicted and, hence, must be determined experimentally.

Figure 22:
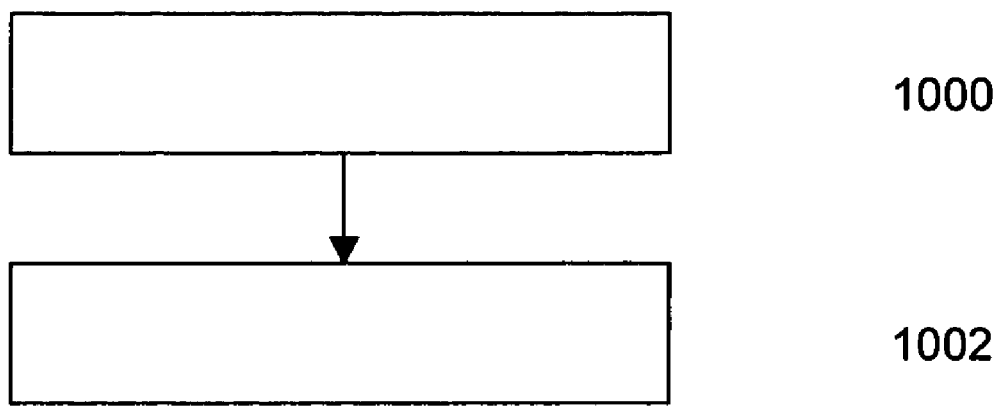
FIG. 22 is a simplified flow diagram of a method of separating ions according to an embodiment of the instant invention; and, FIG. 23 is a simplified flow diagram of another method of separating ions according to an embodiment of the instant invention.

Referring now to FIG. 22, shown is a simplified flow diagram of a method of separating ions according to an embodiment of the instant invention. At step 1000, a FAIMS analyzer is provided, the FAIMS having an analyzer region defined by a space between a first electrode surface and a second electrode surface, to effect a separation of a subset of ions from an ionized sample. At step 1002, a temperature gradient is established within the analyzer region between the first electrode surface and the second electrode surface in dependence of a desired separation. As discussed above in reference to FIG. 21 the desired separation is selected according to the requirements of transmission efficiency and CV peak widths for the application and particular type of ion analysis being performed.

Figure 23:
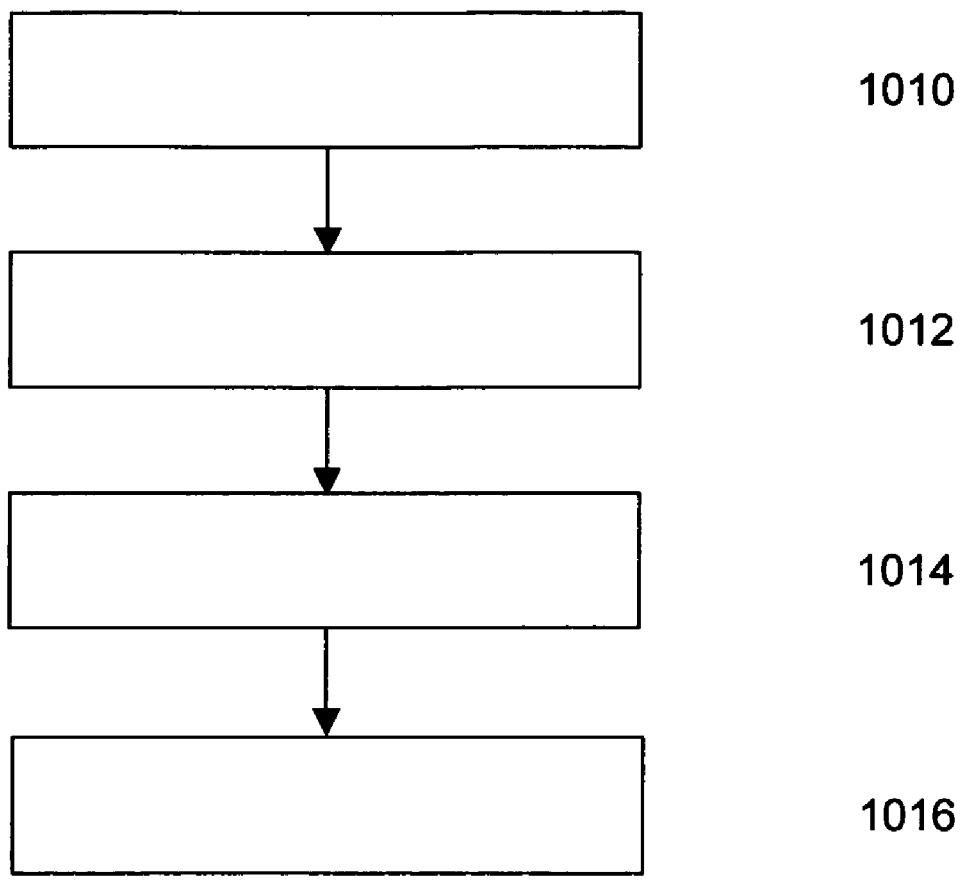

Referring now to FIG. 23 shown is a simplified flow diagram of a method of separating ions according to another embodiment of the instant invention. At step 1010, a FAIMS analyzer region is provided, the FAIMS analyzer region defined by a space between a first electrode surface and a second electrode. At step 1012, a gas is provided in the FAIMS analyzer region. At step 1014 a temperature gradient is established across the FAIMS analyzer region between the first electrode surface and the second electrode surface, to produce an ion focusing condition in the FAIMS analyzer region different from an ion focusing condition absent the temperature gradient. At step 2016, the produced ion focusing condition is used while transmitting an ion of interest through the FAIMS analyzer region. As discussed above the temperature gradient may be selected to modify the E/N gradient in a FAIMS having an electrode geometry that inherently exhibits an E/N gradient or to generate an E/N gradient in a FAIMS having an electrode geometry which previously did not exhibit an E/N gradient.

Numerous other embodiments may be envisaged without departing from the spirit and scope of the invention.

What is claimed is:

1. An apparatus for separating ions, comprising:
a FAIMS analyzer region defined by a space between a first electrode surface and a second electrode surface, the FAIMS analyzer region having a width defined by a distance between the first electrode surface and the second electrode surface;
a gas inlet for introducing a gas into the FAIMS analyzer region; and,
a temperature controller in thermal communication with at least one of the first electrode surface, the second electrode surface and the gas for controllably establishing a temperature gradient across the width of the FAIMS analyzer region.

2. An apparatus according to claim 1, wherein during use a temperature of the gas varies across the width of the FAIMS analyzer region between a first temperature adjacent to the first electrode surface and a second temperature adjacent to the second electrode surface, wherein the first temperature and the second temperature are different.

3. An apparatus according to claim 1, wherein the first electrode surface is a curved outer surface of a cylindrically-shaped inner electrode and the second electrode surface is a curved inner surface of an outer electrode.

4. An apparatus according to claim 3, wherein the temperature controller comprises a heat-exchange passage defined within a portion of the inner electrode, for conducting a flow of a heat exchange fluid through the portion of the inner electrode.

5. An apparatus according to claim 4, wherein during use the heat exchange fluid is in the gas phase.

6. An apparatus according to claim 4, wherein during use the heat exchange fluid is in the liquid phase.

7. An apparatus according to claim 4, wherein the temperature controller comprises a heat-exchange passage defined within a portion of the outer electrode, for conducting a flow of a heat exchange fluid through the portion of the outer electrode.

8. An apparatus according to claim 3, comprising an electrically insulating block disposed for supporting the inner electrode and the outer electrode such that the inner electrode is spaced-apart from the outer electrode, the electrically insulating block being in thermal communication with at least one of the inner electrode and the outer electrode, wherein the temperature controller comprises a heat-exchange passage defined within a portion of the electrically insulating block, for conducting a flow of a heat exchange fluid through the portion of the electrically insulating block.

9. An apparatus according to claim 8, wherein the temperature controller comprises a heat-exchange passage defined within a portion of the inner electrode, for conducting a flow of a heat exchange fluid through the portion of the inner electrode.

10. An apparatus according to claim 8, wherein the temperature controller comprises a heat-exchange passage defined within a portion of the outer electrode, for conducting a flow of a heat exchange fluid through the portion of the outer electrode.

11. An apparatus according to claim 1, wherein the first electrode surface is a non-curved electrode surface portion and the second electrode surface is a non-curved electrode surface portion disposed in a spaced-apart facing and approximately parallel arrangement with the first electrode surface.

12. An apparatus according to claim 1, wherein the temperature controller is in thermal communication with the first electrode surface for controllably affecting the temperature of the first electrode surface to be different from a temperature of the second electrode surface.

13. A method of separating ions, comprising:
providing a FAIMS analyzer region defined by a space between a first electrode surface and a second electrode surface; and,
establishing a temperature gradient across the FAIMS analyzer region between the first electrode surface and the second electrode surface, for affecting ion focusing within the FAIMS analyzer region.

14. A method according to claim 13, comprising effecting a separation of a subset of ions from an ionized sample within the FAIMS analyzer region, wherein the subset of ions is focused differently compared to a separation that is effected absent the established temperature gradient across the FAIMS analyzer region.

15. A method according to claim 13, comprising;
introducing ions into an ion inlet end of the analyzer region; and,
effecting a separation of the ions based on an ion mobility property of the ions, to transmit an ion of interest through the analyzer region between the ion inlet end and an ion outlet end thereof.

16. A method according to claim 13, comprising:
providing a gas into the FAIMS analyzer region; and,
controllably affecting a first temperature of the gas adjacent to the first electrode surface and a second temperature of the gas adjacent to the second electrode surface, wherein the first temperature and the second temperature are different.

17. A method according to claim 13, wherein the first electrode surface defines a surface of a first electrode body, and comprising conducting a flow of a heat exchange fluid through a heat exchange passage that is defined within the first electrode body, so as to affect the temperature of the first electrode surface.

18. A method according to claim 17, comprising adjusting a temperature of the heat exchange fluid to a predetermined temperature prior to conducting the heat exchange fluid through the heat exchange passage, the predetermined temperature being selected for establishing the temperature gradient within the analyzer region between the first electrode surface and the second electrode surface.

19. A method according to claim 18, wherein the heat exchange fluid at the predetermined temperature is in the gas phase.

20. A method according to claim 18, wherein the heat exchange fluid at the predetermined temperature is in the liquid phase.

21. A method according to claim 13, wherein the temperature gradient is established to produce an ion-focusing condition within the FAIMS analyzer region that is different from an ion-focusing condition absent the temperature gradient.

22. A method according to claim 21, wherein the temperature gradient is selected to produce an ion-focusing condition of increased ion focusing compared to the ion-focusing condition absent the temperature gradient.

23. A method according to claim 21, wherein the temperature gradient is selected to produce an ion-focusing condition of decreased ion focusing compared to the ion-focusing condition absent the temperature gradient.

24. A method according to claim 21, wherein the ion-focusing condition absent the temperature gradient is an absence of ion focusing.

25. A method according to claim 13, comprising:
providing a heat exchanger adjacent to and in thermal communication with at least one of the first electrode surface and the second electrode surface; and,
exchanging heat between the heat exchanger and the at least one of the first electrode surface and the second electrode surface.

26. A method according to claim 25, wherein exchanging heat between the heat exchanger and the at least one of the first electrode surface and the second electrode surface comprises transferring heat from the heat exchanger to the at least one of the first electrode surface and the second electrode surface.

27. A method according to claim 25, wherein exchanging heat between the heat exchanger and the at least one of the first electrode surface and the second electrode surface comprises transferring heat to the heat exchanger from the at least one of the first electrode surface and the second electrode surface.

* * * * *